(12) United States Patent
Marcin et al.

(10) Patent No.: US 7,084,178 B2
(45) Date of Patent: Aug. 1, 2006

(54) ANTIAMYLOID PHENYLSULFONAMIDES: N-CYCLOALKYLCARBOXAMIDES DERIVATIVES

(75) Inventors: Lawrence R. Marcin, Bethany, CT (US); Mendi A. Higgins, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 68 days.

(21) Appl. No.: 10/992,455

(22) Filed: Nov. 18, 2004

(65) Prior Publication Data

US 2005/0113442 A1 May 26, 2005

Related U.S. Application Data

(60) Provisional application No. 60/525,350, filed on Nov. 26, 2003.

(51) Int. Cl.
- A61K 31/415 (2006.01)
- A61K 31/38 (2006.01)
- A61K 31/275 (2006.01)
- A61K 31/20 (2006.01)
- A61K 31/18 (2006.01)

(52) U.S. Cl. ............ 514/604; 514/406; 514/438; 514/445; 514/522; 514/530; 514/538; 514/542; 548/371.2; 558/413; 549/68; 549/77; 560/12; 560/13; 564/89; 564/90

(58) Field of Classification Search .......... 514/406, 514/438, 445, 522, 530, 538, 542, 604; 548/371.1; 549/65, 77; 558/413; 560/12, 13; 564/89, 564/90

See application file for complete search history.

(56) References Cited

U.S. PATENT DOCUMENTS

| 5,276,169 A | 1/1994 | Kunisch et al. ............ 549/480 |
| 5,321,042 A | 6/1994 | Mittendorf et al. ......... 514/447 |
| 5,631,291 A | 5/1997 | Mittendorf et al. ......... 514/561 |
| 5,739,160 A | 4/1998 | Mittendorf et al. ......... 514/510 |
| 5,770,622 A | 6/1998 | Mittendorf et al. ......... 514/561 |
| 5,962,724 A | 10/1999 | Mittendorf et al. ......... 560/121 |

FOREIGN PATENT DOCUMENTS

| DE | 19548825 A1 | 12/1995 |
| WO | WO 95/19337 | 7/1995 |
| WO | WO 00/46189 | 8/2000 |

OTHER PUBLICATIONS

W.L.F. Armarego, et al, "Quinazolines. Part XX. Synthesis and Stereochemistry of N-Methyl-cis-Perhydroquinazolin-2-Ones and N-Methyl-cis-Perhydroquinazolines; a New Conformation for cis-Perhydroquinazolines," J. Chem. Soc. Perkin Trans. 1, pp. 2313-2319, 1974.

J.I. Levin, et al, "Heteroaryl and Cycloalkyl Sulfonamide Hydroxamic Acid Inhibitors of Matrix Metalloproteinases," Bioorganic & Medicinal Chemistry Letters, 11, pp. 239-242, 2001.

Preiml, M., et al, "A New Approach to β-Amino Acids: Biotransformation of N-Protected β-Amino Nitriles," Tetrahedron Letters, 44, pp. 5057-5059, 2003.

Primary Examiner—Peter O'Sullivan
(74) Attorney, Agent, or Firm—James Epperson

(57) ABSTRACT

A series of N-cycloalkylcarboxamide derivatives of N-benzyl benzenesulfonamides of Formula I are described.

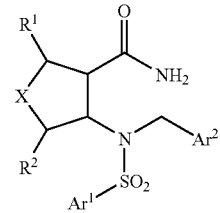

The compounds inhibit β-amyloid peptide (β-AP) production and are useful in the treatment of Alzheimer's Disease and other conditions characterized by aberrant extracellular deposition of β-amyloid. Pharmaceutical compositions and methods of treatment using these compounds are also disclosed.

8 Claims, No Drawings

ANTIAMYLOID PHENYLSULFONAMIDES: N-CYCLOALKYLCARBOXAMIDES DERIVATIVES

CROSS-REFERENCE TO RELATED APPLICATIONS

This application claims the benefit of U.S. Provisional Application Ser. No. 60/525,350 filed Nov. 26, 2003.

This invention encompasses novel N-cycloalkylcarboxamide derivatives of N-benzyl benzenesulfonamides, their pharmaceutical compositions, and methods of use. The compounds inhibit β-amyloid peptide (β-AP) production, thereby acting to prevent the accumulation of amyloid protein deposits in the brain. The compounds are useful for treating conditions responsive to aberrant accumulation of amyloid such as Alzheimer's Disease (AD) and Down's syndrome.

BACKGROUND OF THE INVENTION

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (greater than $100 billion annually in the U.S.) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. There is currently no effective treatment.

There have been many theories relating to the etiology and pathogenesis of AD. These theories were either based on analogies with other diseases and conditions (e.g., slow virus and aluminum theories), or based on pathologic observations (e.g., cholinergic, amyloid, or tangle theories). Genetic analysis can potentially differentiate between competing theories. The identification of mutations in the β-amyloid precursor protein (β-APP) of individuals prone to early onset forms of AD and related disorders strongly supports the amyloidogenic theories.

The β-amyloid precursor protein (β-APP), a large membrane spanning glycoprotein found in tissues of mammals, including humans, is encoded by a gene on the long arm of human chromosome 21. The main constituent of the plaques, tangles and amyloid deposits is known to be β-amyloid peptides (β-AP), composed of approximately 39 to 43 amino acid fragments of β-APP, and in particular, the 40 amino acid fragment known as Aβ1-40. Several lines of evidence support the involvement of β-AP in the pathogenesis of AD lesions. β-AP and related fragments have been shown to be toxic for PC-12 cell lines and primary cultures of neurons, as well as causing neuronal degeneration with accompanying amnesia in rodents. Strong evidence for the role of β-AP in AD consists of observations of genetic β-APP mutations in individuals with certain forms of Familial Alzheimer's Disease (FAD) and the correlation of disease onset with altered release of β-AP fragments.

It is presently believed that the development of amyloid plaques in the brains of AD patients is a result of excess production and/or reduced clearance or removal of β-AP. It is known that a basal level of β-AP production may be a normal process and that multiple pathways for cleavage of β-APP exist. Currently, however, it is unclear which classes of proteinases or inhibitors thereof that would be effective in treating AD. Various peptidergic compounds and their pharmaceutical compositions have been disclosed as useful in inhibiting or preventing amyloid protein deposits in brains of AD and Down's Syndrome patients.

N-cycloalkyl benzenesulfonamides have been disclosed. See, for example, the following patents and publications: Hermann, R. German patent 195 48 825 A1, 1995; Mittendorf, J. et al. U.S. Pat. No. 5,962,724, 1999; Mittendorf, J. et al. U.S. Pat. No. 5,770,622, 1998; Mittendorf, J. et al. U.S. Pat. No. 5,631,291, 1997; Mittendorf, J. et al. U.S. Pat. No. 5,739,160, 1998; Mittendorf, J. et al. U.S. Pat. No. 5,321,042, 1994; Kunisch, F. et al. U.S. Pat. No. 5,276,169, 1994; Mittendorf, J. et al. PCT patent application WO 95/19337, 1995; Watanabe, F. and Hiroshige, T. PCT patent application, WO 00/46189, 2000; Armarego, W. L. F. and Reece, P. A. *J. Chem. Soc. Perkin Trans.* 1 1974, 2313; and Levin, J. I. et al. *Bioorganic Med. Chem. Lett.* 2001, 11, 239. Nothing in these references teaches or suggests the novel compounds of this invention or their use as inhibitors of β-AP production.

DESCRIPTION OF THE INVENTION

The invention encompasses a series of N-cycloalkylcarboxamide derivatives of N-benzyl benzenesulfonamides of Formula I. The compounds inhibit γ-secretase, decreasing the formation of β-amyloid peptide (β-AP) from β-amyloid precursor protein (β-APP). The pharmacologic action of these compounds makes them useful for treating conditions responsive to the inhibition of β-AP, for example, Alzheimer's Disease (AD) and Down's Syndrome. Pharmaceutical compositions and methods of treatment are also described.

One aspect of the invention is a compound of Formula I

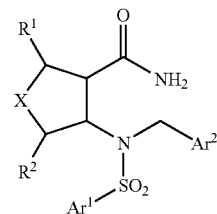

wherein:

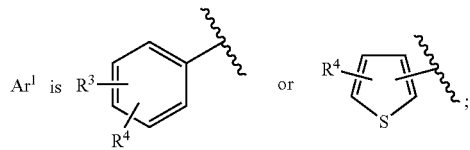

-continued

Ar² is 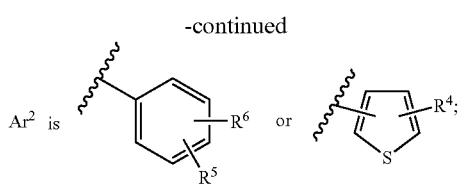

X is methylene, ethylene, propylene, 1,2-ethenediyl, or 1,2-cyclopropanediyl;
R¹ and R² are independently hydrogen or $C_{1-6}$alkyl or taken together are methylene or ethylene;
R³ is halogen;
R⁴ is hydrogen or halogen;
R⁵ is halogen, $C_{1-6}$alkyl, $C_{1-3}$alkoxy, $C_{1-3}$hydroxyalkyl, trifluoromethyl, trifluoromethoxy, trifluoromethylthio, cyano, $CO_2R^7$, $CONR^8R^9$, $NR^8R^9$, or $N(R^7)COR^7$;
R⁶ is hydrogen, halogen, $C_{1-6}$alkyl, $C_{1-3}$alkoxy, cyano, trifluoromethyl, or trifluoromethoxy;
R⁷ is hydrogen or $C_{1-6}$alkyl; and
R⁸ and R⁹ are independently hydrogen or $C_{1-6}$alkyl;

or a pharmaceutically acceptable salt or solvate thereof.

"Alkyl," "alkoxy" and "hydroxyalkyl" include straight and branched chain configuratons. 1,2-Ethenediyl means —CH═CH—. 1,2-Cyclopropanediyl means

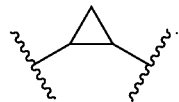

Trifluoromethylthio means $CF_3S$—.

As some Formula I compounds possess asymmetric atoms, the invention includes all stereoisomeric forms of the compounds. The use of a designations such as (R) or (S), as shown below, are intended to include mostly one stereoisomer. Mixtures of isomers can be separated into individual isomers according to methods which are known in the art, for example, chiral HPLC, fractional crystallization, adsorption chromatography and other suitable separation processes. Racemates can be separated into antipodes by methods known in the art, for example, after introduction of suitable salt-forming groupings (forming a mixture of diastereosiomeric salts with optically active salt-forming agents), separating the mixture into diastereomeric salts and converting the separated salts into the free compounds. The possible enantiomeric forms may also be separated by fractionation through chiral high pressure liquid chromatography columns.

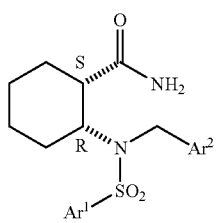

The invention includes all pharmaceutically acceptable salt forms of the instant compounds. Pharmaceutically acceptable salts are those in which the counter ions do not contribute significantly to the physiological activity or toxicity of the compounds and as such function as pharmacological equivalents. The salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the instant compounds. Solvates do not contribute significantly to the physiological activity or toxicity of the compounds and as such function as pharmacological equivalents. Solvates may form in stoichiometric amounts or may form with adventitious solvent or a combination of both. One type of solvate is hydrate and some hydrated forms include monohydrate, hemihydrate, and dihydrate.

Another aspect of the invention are compounds of Formula I where Ar¹ is

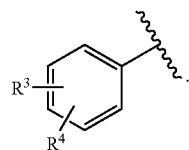

Another aspect of the invention are compounds of Formula I where Ar¹ is

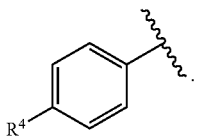

Another aspect of the invention are compounds of Formula I where Ar¹ is 4-chlorophenyl.

Another aspect of the invention are compounds of Formula I where R¹ and R² are hydrogen and X is ethylene.

Another aspect of the invention are compounds of Formula Ia.

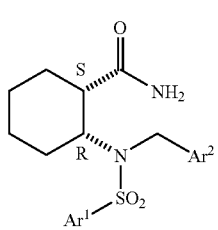

Ia

Another aspect of the invention are compounds of Formula I where R¹ and R² are independently hydrogen or methyl.

Some compounds of the invention:
4-[[(1R,2S)-(2-carbamoyl-cyclohexyl)-(4-chloro-benzenesulfonyl)-amino]-methyl]-benzoic acid methyl ester;
4-[[(1R,2S)-(2-carbamoyl-cyclohexyl)-(4-chloro-benzenesulfonyl)-amino]-methyl]-N-ethyl-benzamide;
(1S,2R)-2-[(4-tert-butyl-benzyl)-(4-chloro-benzenesulfonyl)-amino]-cyclohexanecarboxylic acid amide;
(1S,2R)-2-[(4-chloro-benzenesulfonyl)-(3-chloro-4-trifluoromethoxy-benzyl)-amino]-cyclohexanecarboxylic acid amide;
(1S,2R)-2-[(4-chloro-benzenesulfonyl)-(3-chloro-4-fluoro-benzyl)-amino]-cyclohexanecarboxylic acid amide;
(1S,2R)-2-[(4-chloro-benzenesulfonyl)-[4-(1-hydroxy-1-methyl-ethyl)-benzyl]-amino]-cyclohexanecarboxylic acid amide;
(1S,2R)-2-[(4-chloro-benzenesulfonyl)-(5-chloro-thiophen-2-ylmethyl)-amino]-cyclohexanecarboxylic acid amide;
(1S,2R)-2-[(4-chloro-benzenesulfonyl)-(4-trifluoromethylsulfanyl-benzyl)-amino]-cyclohexanecarboxylic acid amide;
cis-2-[(4-chloro-benzenesulfonyl)-(4-trifluoromethoxy-benzyl)-amino]-cyclohexanecarboxylic acid amide;
cis-2-[(4-chloro-benzenesulfonyl)-(4-trifluoromethyl-benzyl)-amino]-cyclohexanecarboxylic acid amide;
cis-2-[(4-chloro-benzenesulfonyl)-(4-fluoro-benzyl)-amino]-cyclohexanecarboxylic acid amide;
cis-2-[(4-chloro-benzenesulfonyl)-(4-cyano-benzyl)-amino]-cyclohexanecarboxylic acid amide;
cis-4-[[(2-carbamoyl-cyclohexyl)-(4-chloro-benzenesulfonyl)-amino]-methyl]-benzoic acid methyl ester;
trans-2-[(4-chloro-benzenesulfonyl)-(4-trifluoromethoxy-benzyl)-amino]-cyclohexanecarboxylic acid amide;
trans-2-[(4-chloro-benzenesulfonyl)-(4-trifluoromethyl-benzyl)-amino]-cyclohexanecarboxylic acid amide;
trans-2-[(4-chloro-benzenesulfonyl)-(4-cyano-benzyl)-amino]-cyclohexanecarboxylic acid amide;
cis-exo-3-[(4-chloro-benzenesulfonyl)-(4-trifluoromethyl-benzyl)-amino]-bicyclo[2.2.1]heptane-2-carboxylic acid amide;
cis-exo-3-[(4-chloro-benzenesulfonyl)-(4-cyano-benzyl)-amino]-bicyclo[2.2.1]heptane-2-carboxylic acid amide;
cis-exo-4-[[(3-carbamoyl-bicyclo[2.2.1]hept-2-yl)-(4-chloro-benzenesulfonyl)-amino]-methyl]-benzoic acid methyl ester;
cis-4-[[(2-carbamoyl-cycloheptyl)-(4-chloro-benzenesulfonyl)-amino]-methyl]-benzoic acid methyl ester;
cis-2-[(4-chloro-benzenesulfonyl)-(4-cyano-benzyl)-amino]-cycloheptanecarboxylic acid amide;
cis-2-[(4-chloro-benzenesulfonyl)-(4-trifluoromethyl-benzyl)-amino]-cycloheptanecarboxylic acid amide;
cis-2-[(4-chloro-benzenesulfonyl)-(4-pyrazol-1-yl-benzyl)-amino]-cycloheptanecarboxylic acid amide;
cis-2-[(4-chloro-benzenesulfonyl)-(4-ethylcarbamoyl-benzyl)-amino]-cycloheptanecarboxylic acid amide;
cis-2-[(4-chloro-benzenesulfonyl)-(4-trifluoromethyl-benzyl)-amino]-cyclopentanecarboxylic acid amide;
cis-2-[(4-chloro-benzenesulfonyl)-(4-cyano-benzyl)-amino]-cyclopentanecarboxylic acid amide;
cis-4-[[(2-carbamoyl-cyclopentyl)-(4-chloro-benzenesulfonyl)-amino]-methyl]-benzoic acid methyl ester;
4-[[(1R,2S)-(2-carbamoyl-cyclohexyl)-(4-chlorobenzenesulfonyl)-amino]-methyl]-N-ethyl benzamide;
4-[[(1S,2S)-(2-carbamoyl-cyclohexyl)-(4-chlorobenzenesulfonyl)-amino]-methyl]-N-ethyl benzamide;
4-[[(1R,2R)-(2-carbamoyl-cyclohexyl)-(4-chlorobenzenesulfonyl)-amino]-methyl]-N-ethyl benzamide;
4-[[(1R,2S)-(2-carbamoyl-cyclopentyl)-(4-chlorobenzenesulfonyl)-amino]-methyl]-N-ethyl-benzamide; and
4-[[(1R,2R)-(2-carbamoyl-cyclopentyl)-(4-chlorobenzenesulfonyl)-amino]-methyl]-N-ethyl-benzamide.

Synthetic Methods

The compounds of the present invention can be made by various methods including the process shown in Scheme 1. Starting materials and reagents are commercially available or known in the literature. Carboxamide intermediates of Formula 3 can be prepared from 2-aminocycloalkylcarboxylic acids (Formula 1) by esterification followed by amination of the resulting ester. Sulfonylation of the amino moiety can be accomplished with a variety of aryl sulfonylchlorides. N-Alkylation of the sulfonamide moiety of the resultant Formula 4 compounds can produce compounds of Formula I.

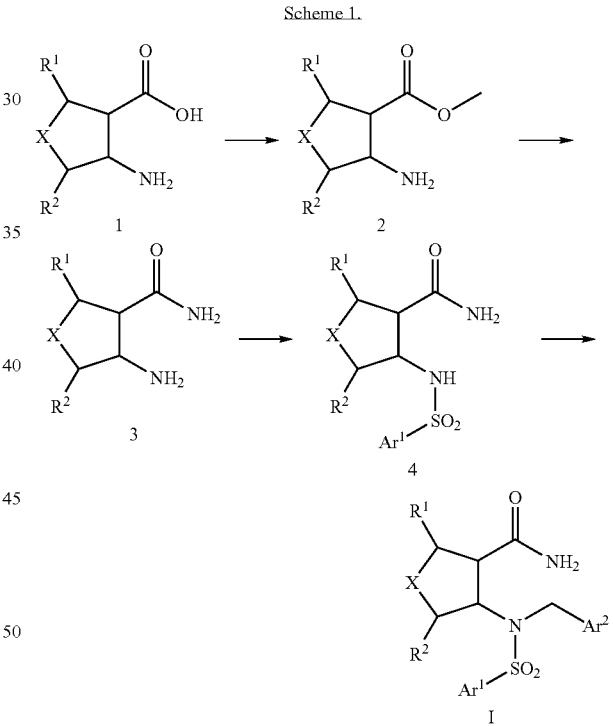

Alternatively, sulfonamide intermediates of Formula 4 can be prepared starting from the corresponding α,β-unsaturated esters of Formula 5, Scheme 2. Conjugate addition of (S)— or (R)—(−)—N-benzyl-α-methylbenzylamine to compounds of Formula 5 can afford the chiral amino esters of Formula 6. Cis/trans equilibration of the esters can be accomplished under basic conditions. Hydrogenolysis of the benzylamines followed by sulfonylation of the resulting primary amine can produce compounds of Formula 7. Saponification of the ester can provide carboxylic acids of Formula 8. Advanced intermediates of Formula 4 can be obtained after routine amidation.

Scheme 2.

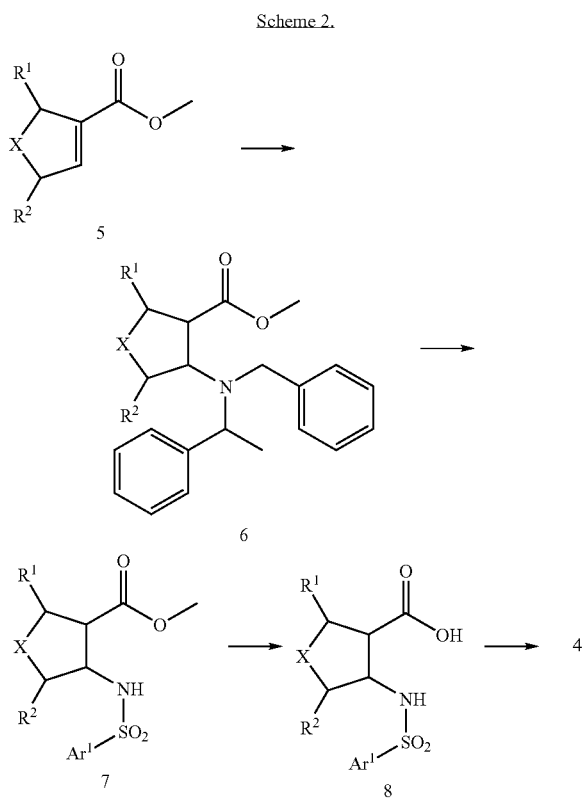

Biological Methods

Competitive in vitro binding assays can be used to identify compounds that inhibit γ-secretase activity. For example, [³H]-Compound A can be used for binding assays with membranes from THP-1 cells (Seiffert, D.; Bradley, J. et al., *J. Biol. Chem.* 2000, 275, 34086–34091). Compound A is (2R,3S) N1-[(3S)-hexahydro-1-(3-phenoxybenzyl)-2-oxo-1H-azepin-3-yl]-2-(2methylpropyl)-3-(propyl)-butanediamide, which is described in U.S. patent U.S. Pat. No. 6,331,408 (Dec. 18, 2001); PCT Publication WO 00/28331; PCT Publication WO 00/07995; and Seiffert, D., Bradley, J. et al., *J. Biol. Chem.* 2000, 275. 34086–34091.

Compound A

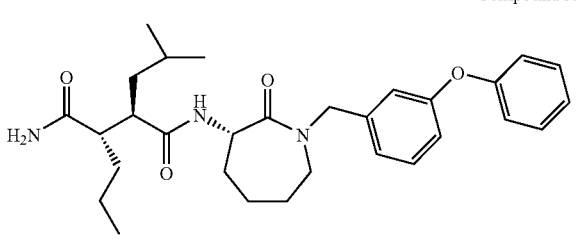

To evaluate the compounds of this invention using this assay, THP-1 cells were grown in spinner cultures in RPMI 1640 containing L-glutamine and 10 μM β-mercaptoethanol to a density of 5×10⁵ cells/ml. Cells were harvested by centrifugation and cell pellets were quick frozen in dry ice/ethanol and stored at −70° C. prior to use. The pellets of approximately 2×10⁴ THP-1 cells were homogenized using a Brinkman Polytron at setting 6 for 10 sec. The homogenate was centrifuged at 48,000×g for 12 min, and the resulting pellet was washed by repeating the homogenization and centrifugation. The final cell pellet was resuspended in buffer to yield a protein concentration of approximately 0.5 mg/ml. Assays were initiated by the addition of 150 μl of membrane suspension to 150 μl of assay buffer containing 0.064 μCi of radioligand and various concentrations of unlabeled compounds. Binding assays were performed in duplicate in polypropylene 96-well plates in a final volume of 0.3 ml containing 50 mM Hepes, pH 7.0, and 5% dimethyl sulfoxide. Nonspecific binding was defined using incubations with 300 nM compound A (Seiffert, D., Bradley, J. et al., *J. Biol. Chem.* 2000, 275, 34086–34091). After incubating at 23° C. for 1.3 hr, bound ligand was separated from free radioligand by filtration over GFF glass fiber filters presoaked in 0.3% ethyleneimine polymer solution. Filters were washed three times with 0.3 ml of ice cold phosphate-buffered saline, pH 7.0, containing 0.1% Triton X-100. Filter-bound radioactivity was measured by scintillation counting. $IC_{50}$ values were then determined and used to calculate $K_i$ values using the Cheng-Prusoft correction for $IC_{50}$ values. Compounds were scored as active γ-secretase inhibitors if $K_i$ values were less than 10 μM.

The compounds of this invention were evaluated in the assay described above, as well as with other evaluation methods, and found to be inhibitors of γ-secretase. Representative examples are summarized in Table 1. In the table, an inhibitory concentration ($IC_{50}$) of less than or equal to 50 nM is represented by +++; between 50 nM and 500 nM by ++; between 500 nM and 10000 nM by +.

TABLE 1

Examples of activity in the in vitro binding assay.

| Example | Binding affinity ($IC_{50}$ in nM) |
|---|---|
| 1 | +++ |
| 2 | +++ |
| 20 | ++ |
| 23 | + |
| 28 | + |
| 29 | ++ |
| 30 | ++ |
| 31 | ++ |
| 32 | + |

Activity ($IC_{50}$): ≦50 nM = +++; 50–500 nM = ++; 500–10000 nM = +.

As the compounds of the invention prevent Aβ-amyloid formation by inhibiting γ-secretase, these compounds or pharmaceutical compositions thereof would useful for treating disorders associated with the abnormal presence of β-amyloid peptide.

γ-Secretase inhibitors can also be evaluated using in vitro assays based on the inhibition of Aβ formation in cultured cells. Cultured human cell lines, such as HEK293 and H4 cells, which express APP and γ-secretase activity or transfected derivative cell lines that overexpress wild-type APP, mutant APP, or APP fusion proteins will secrete Aβ peptides into the culture media that can be quantified as previously outlined (Dovey, H., John, V. et al., J. Neurochem. 2001, 76, 173–181). The incubation of these cultured cells with γ-secretase inhibitors decreases the production of Aβ peptides. For instance, H4 cells stably transfected to overexpress the HPLAP-APP fusion protein described above were grown as above, detached, and adjusted to 2×10⁵ cells/ml.

100 µl of the resulting suspension was then added to each well of a 96-well plate. After 4 hrs, the media was removed and replaced with 100 µl serum-free media containing various dilutions of the test compound. Plates were then incubated for 18 hrs at 37° C. and a 100 µl aliquot of the tissue culture supernatant was removed for determination of Aβ levels using time-resolved fluorescence of the homogenous sample as outlined above. Alternately, the other methods described above for Aβ determination could be used. The extent of Aβ inhibition was used to calculate the $IC_{50}$ value for the test compound. Compounds of the present invention are considered active when tested in the above assay if the $IC_{50}$ value for the test compound is less than 50 µM.

Examples of the results obtained when the invention compounds are subjected to the above described assay are shown in Table 2. In Table 2, an inhibitory concentration ($IC_{50}$) of less than or equal to 50 nM is represented by +++; between 50 nM and 500 nM by ++; between 500 nM and 50000 nM by +.

TABLE 2

Inhibition of β-amyloid peptide formation in human H4 cells.

| Example | Inhibition of Aβ in cells ($IC_{50}$ in nM) |
|---|---|
| 1 | +++ |
| 2 | +++ |
| 3 | ++ |
| 4 | ++ |
| 5 | ++ |
| 6 | +++ |
| 7 | +++ |
| 8 | +++ |
| 10 | ++ |
| 13 | +++ |
| 21 | + |
| 24 | +++ |

Activity ($IC_{50}$): ≦50 nM = +++; 50–500 nM = ++; 500–50000 nM = +.

In addition to cleaving APP, γ-secretase cleaves other substrates. These include the Notch family of transmembrane receptors (reviewed in: Selkoe, D. *Physiol. Rev.* 2001, 81, 741–746; Wolfe, M. J. *Med. Chem.* 2001 44, 2039–2060); LDL receptor-related protein (May, P., Reddy, Y. K., Herz, J. *J. Biol. Chem.* 2002, 277, 18736–18743); ErbB-4 (Ni, C. Y., Murphy, M. P., Golde, T. E., Carpenter, G. *Science* 2001, 294, 2179–2181); E-cadherin (Marambaud, P., Shioi, J., et al., *EMBO J.* 2002, 21, 1948–1956); and CD44 (Okamoto, I., Kawano, Y., et al., *J. Cell Biol.* 2001, 155, 755–762). If inhibition of cleavage of non-APP substrates causes undesirable effects in humans, then desired γ-secretase inhibitors would preferentially inhibit APP cleavage relative to unwanted substrates. Notch cleavage can be monitored directly by measuring the amount of cleavage product or indirectly by measuring the effect of the cleavage product on transcription (Mizutani, T., Taniguchi, Y., et al. *Proc. Natl. Acad. Sci. USA* 2001, 98, 9026–9031).

Pharmaceutical Compositions and Methods of Treatment

Another aspect of this invention includes pharmaceutical compositions comprising at least one compound of Formula I in combination with a pharmaceutical adjuvant, carrier or diluent.

Another aspect of this invention relates to a method of treatment of disorders characterized by aberrant extracellular deposition of amyloid and which are responsive to the inhibition of β-amyloid peptide in a mammal in need thereof, which comprises administering to said mammal a therapeutically effective amount of a compound of Formula I or a nontoxic pharmaceutically acceptable salt, solvate or hydrate thereof.

Another aspect of this invention relates to a method for treating systemic (vascular) amyloidosis, pulmonary or muscle amyloidosis, Alzheimer's Disease, Down's Syndrome, or other diseases characterized by extracellular amyloid deposition in a mammal in need thereof, which comprises administering to said mammal a therapeutically effective amount of a compound of Formula I or a non-toxic pharmaceutically acceptable salt, solvate or hydrate thereof.

In the method of the present invention, the term "therapeutically effective amount" means the total amount of each active component of the method that is sufficient to show a meaningful patient benefit, i.e., improve one or more clinical parameters of disease activity, e.g. retention or cognition; or improve disease symptoms such as anxiety or neuromotor control. The subject amount is further characterized by inhibition of β-amyloid peptide production as determined using in vitro assays or in vivo animal models of disease. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means ameliorating one or more clinical indicia of disease activity in a patient having a disease associated with β-amyloid peptide.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of β-AP inhibition desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition related to aberrant production and/or extracellular deposition of β-AP as described herein, generally the daily dose will be from about 0.05 mg/kg to about 10 mg/kg and preferably, about 0.1 to 2 mg/kg when administered parenterally. For oral administration, the dose may be in the range from about 1 to about 50 mg/kg and preferably from 0.1 to 2 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the meaning of the invention.

DESCRIPTION OF SPECIFIC EMBODIMENTS

In the following examples, all temperatures are given in degrees Centigrade. Melting points were recorded on a Gallenkamp capillary melting point apparatus and are uncorrected. Proton magnetic resonance ($^1$H NMR) spectra were recorded on a Bruker AC 300. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) or sodium chloride film were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Optical rotations [α]$_D^{25}$ were determined on a Perkin-Elmer 41 polarimeter in the solvents indicated. Low resolution mass spectra (MS) and the apparent molecular (MH$^+$) or (M–H)$^+$ was determined on a Finnigan TSQ 7000. The elemental analysis are reported as percent by weight.

Intermediates (1S,2R)-2-aminocyclohexanecarboxylic acid. A mixture of (+)-(1S,2R)-2-benzamidocyclohexanecarboxylic acid (4.0 g, 16.2 mmol, TCI chemical company) and 6 M hydrochloric acid (200 mL) was heated at reflux for 48 h. The reaction mixture was cooled to room temperature and extracted with diethyl ether (2×200 mL). The aqueous portion was concentrated in vacuo to afford (1S,2R)-2-aminocyclohexanecarboxylic acid as a white solid. The crude product was used in the next step without purification or characterization.

cis-2-aminocycloheptanecarboxylic acid. Chlorosulfonylisocyanate (11.0 g, 77.9 mmol) in methylene chloride (4 mL) was added dropwise to cycloheptene in methylene chloride (50 mL), then heated to reflux for 10 h. The mixture was quenched by dropwise addition of water then extracted with methylene chloride (2×). The combined organic layers were washed with water (1×), brine (1×) and then dried over sodium sulfate. The solvent was removed in vacuo and the residue diluted with ether (30 mL). The ether solution was added dropwise to a solution of 10% sodium sulfite/ether (2:1, 150 mL) maintaining the pH between 7 and 8 with 10% sodium hydroxide. After the addition was completed, stirring was continued for 3 h then the reaction was extracted with ether (3×). The combined organic layers were washed with water (1×), brine (1×) and then dried over sodium sulfate. The solvent was evaporated in vacuo to provide 2.45 g of cis-2-amino-cycloheptanecarboxylic acid as a colorless oil. The crude acid was used directly in the next reaction: $^1$H NMR (400 MHz, CDCl$_3$) δ 5.87 (s br, 3 H), 3.81 (m, 1 H), 3.30 (m, 1 H), 1.90–1.29 (m, 10 H).

Intermediates of Formula 2

(1S,2R)-2-aminocyclohexanecarboxylic acid methyl ester. Thionyl chloride (4.73 mL, 64.8 mmol) was slowly added to a chilled (ice-water bath) suspension of (1S,2R)-2-aminocyclohexanecarboxylic acid (16.2 mmol) in anhydrous methanol (200 mL). After complete addition, the cold bath was removed and the resulting mixture warmed to room temperature. After 24 h, the reaction mixture was evaporated to dryness under a stream of dry nitrogen. The crude product, (1S,2R)-2-aminocyclohexanecarboxylic acid methyl ester, was obtained as a white solid and used in the next step without purification or characterization.

cis-2-aminocyclohexanecarboxylic acid methyl ester. Thionyl chloride (5.48 g, 46.1 mmol) was added dropwise to a solution of cis-2-aminocyclohexanecarboxylic acid (2.0 g, 14.0 mmol) in methanol (50 mL) at 0° C. The mixture was allowed to warm to room temperature and stir for 18 h. The clear solution was then evaporated to dryness, and the residual volatiles were removed on high vacuum. The crude product, cis-2-aminocyclohexanecarboxylic acid methyl ester, was isolated in quantitative yield and used in the next reaction without purification: $^1$H NMR (400 MHz, CDCl$_3$) δ 8.50 (s br, 2 H), 3.78 (s, 3 H), 3.59 (s br, 1 H), 3.18 (s br, 1 H), 2.27 (m, 1 H), 2.08 (m, 1 H), 1.88 (m, 2 H), 1.45 (m, 4 H).

trans-2-aminocyclohexanecarboxylic acid methyl ester. Commercially available trans-2-aminocyclohexanecarboxylic acid (1.0 g, 6.98 mmol) was converted to trans-2-aminocyclohexanecarboxylic acid methyl ester (1.40 g crude weight) according to the method described for the preparation of cis-2-aminocyclohexanecarboxylic acid methyl ester. The crude product was used in the next reaction without purification: $^1$H NMR (400 MHz, DMSO-d$_6$) δ 8.06 (s br, 2 H), 3.67 (s, 3 H), 3.19 (m, 1 H), 2.47 (m, 1 H), 1.95 (m, 2 H), 1.68 (m, 2 H), 1.30 (m, 4 H).

cis-exo-3-aminobicyclo[2.2.1]heptane-2-carboxylic acid methyl ester. Commercially available cis-exo-3-aminobicyclo[2.2.1]heptane-2-carboxylic acid (1.0 g, 6.44 mmol) was converted to cis-exo-3-aminobicyclo[2.2.1]heptane-2-carboxylic acid methyl ester (1.28 g crude weight) according to the method described for the preparation of cis-2-aminocyclohexanecarboxylic acid methyl ester. The crude product was used in the next reaction without purification: $^1$H NMR (400 MHz, CDCl$_3$) δ 8.44 (s br, 2 H), 3.77 (s, 3 H), 3.59 (s br, 1 H), 2.78 (m, 2 H), 2.57 (s, 1 H), 2.12 (m, 1 H), 1.63 (m, 2 H), 1.30 (m, 3 H).

cis-2-aminocycloheptanecarboxylic acid methyl ester. Chlorotrimethylsilane (3.96 mL, 31.2 mmol) was added dropwise to cis-2-aminocycloheptanecarboxylic acid (2.45 g, 15.6 mmol) in methanol (25 mL) at room temperature under nitrogen. After stirring for 2 h, the solvent was evaporated in vacuo and the residue was triturated with ether. The white solid was filtered and then dried under vacuum overnight to provide (1.65 g) cis-2-aminocycloheptanecarboxylic acid methyl ester: $^1$H NMR (CDCl$_3$) δ 8.44 (s br, 2 H), 3.77 (s, 3 H), 3.62 (s br, 1 H), 3.27 (s br, 1 H), 2.20 (m, 2 H), 1.71 (m, 2 H), 1.66–1.47 (m, 6 H); MS m/e 172.26 (M+H)$^+$.

cis-2-aminocyclopentanecarboxylic acid methyl ester. Commercially available cis-2-aminocyclopentanecarboxylic acid (1.0 g, 7.74 mmol) was converted to cis-2-aminocyclopentanecarboxylic acid methyl ester (1.10 g crude weight) according to the method described for the preparation of cis-2-amino-cyclohexanecarboxylic acid methyl ester. The crude product was used in the next reaction without purification: $^1$H NMR (400 MHz, CDCl$_3$) δ 8.51 (s br, 2 H), 3.89 (s br, 1 H), 3.79 (s, 3 H), 3.03 (s br, 1 H), 2.15 (m, 5 H), 1.74 (m, 1 H).

Intermediates of Formula 3

(1S,2R)-2-aminocyclohexanecarboxylic acid amide. A mixture of (1S,2R)-2-aminocyclohexanecarboxylic acid methyl ester (16.2 mmol) and aqueous ammonia (28%, 50 mL) was stirred at room temperature for 24 h. The reaction mixture was concentrated to dryness in vacuo. The residue was suspended in toluene (200 mL) and reconcentrated to afford (1S,2R)-2-aminocyclohexanecarboxylic acid amide as a white solid. The crude product was used in the next step without purification or characterization.

cis-2-aminocyclohexanecarboxylic acid amide. cis-2-Aminocyclohexanecarboxylic acid methyl ester (2.20 g, 14.0 mmol) was treated with aqueous ammonium hydroxide (40 mL) in toluene (40 mL) and stirred vigorously at room temperature for 16 h. The reaction was concentrated to dryness in vacuo and azeotroped with toluene (50 mL). The crude product, cis-2-aminocyclohexanecarboxylic acid amide, was used in the next reaction without purification: $^1$H NMR (400 MHz, DMSO-d$_6$) δ 7.78 (2 H, s br), 7.67 (s, 1 H), 7.25 (s, 1 H), 1.87 (m, 2 H), 1.60 (m, 4 H), 1.41 (m, 4 H).

trans-2-aminocyclohexanecarboxylic acid amide. trans-2-Aminocyclohexanecarboxylic acid methyl ester was converted to trans-2-Aminocyclohexanecarboxylic acid amide (1.44 g crude weight) according to the method described for the preparation of cis-2-aminocyclohexanecarboxylic acid amide. The crude product was used in the next reaction without purification: $^1$H NMR (400 MHz, DMSO-d$_6$) δ 7.69 (m, 3 H), 7.13 (s, 1 H), 3.08 (m, 1 H), 2.32 (m, 1 H), 1.98 (m, 2 H), 1.67 (m, 2 H), 1.24 (m, 4 H).

cis-exo-3-Aminobicyclo[2.2.1]heptane-2-carboxylic acid amide. cis-exo-3-Aminobicyclo[2.2.1]heptane-2-carboxylic acid methyl ester (6.44 mmol) was converted to cis-exo-3-Aminobicyclo[2.2.1]heptane-2-carboxylic acid amide according to the method described for the preparation of cis-2-aminocyclohexanecarboxylic acid amide. The crude product obtained in quantitative yield was used in the next reaction without purification: $^1$H NMR (400 MHz, DMSO-d$_6$) δ 7.77 (s br, 3 H), 7.17 (s, 1 H), 3.21 (m, 1 H), 2.29 (m, 2 H), 1.97 (m, 1 H), 1.51 (m, 2 H), 1.16 (m, 4 H).

cis-2-aminocycloheptanecarboxylic acid amide. cis-2-Aminocycloheptanecarboxylic acid methyl ester (1.65 g, 9.64 mmol) was treated with 20 mL of NH$_4$OH/H$_2$O and stirred at room temperature for 24 h. The solution was concentrated in vacuo and azeotroped once with toluene. The reaction afforded 2.20 g of cis-2-aminocycloheptanecarboxylic acid amide as a white solid: $^1$H NMR (DMSO-d$_6$) δ 7.81 (m, 3 H), 7.20 (s, 1 H), 2.76 (m, 1 H), 1.68–1.40 (m, 11 H); MS m/e 157.28 (M+H)$^+$.

cis-2-aminocyclopentanecarboxylic acid amide. cis-exo-3-Aminobicyclo[2.2.1]heptane-2-carboxylic acid methyl ester (7.74 mmol) was converted to cis-2-aminocyclopentanecarboxylic acid amide according to the method described for the preparation of cis-2-aminocyclohexanecarboxylic acid amide. The crude product obtained in quantitative yield was used in the next reaction without purification: $^1$H NMR (400 MHz, DMSO-d$_6$) δ 7.92 (s br, 2 H), 7.77 (s, 1 H), 7.22 (s, 1 H), 3.58 (m, 1 H), 2.79 (m, 1 H), 1.83 (m, 5 H), 1.58 (m, 1 H).

Intermediates of Formula 4

(1S,2R)-2-(4-chlorobenzenesulfonylamino)-cyclohexanecarboxylic acid amide. A mixture of (1S,2R)-2-aminocyclohexanecarboxylic acid amide (16.2 mmol), 4-chlorobenzenesulfonylchloride (6.84 g, 32.4 mmol), and triethylamine (20 mL, 143 mmol) were stirred in dichloromethane/DMF (500 mL/100 mL) at room temperature for 6 h. The crude mixture was poured into 1 M hydrochloric acid (500 mL). The organic layer was collected and washed with with water (2×500 mL). Hexanes (50 mL) were added to the organic layer. The combined mixture was sequentially washed with water (500 mL) and brine (50 mL). The organic layer was dried (magnesium sulfate), filtered, and concentrated in vacuo. The crude material was purified by silica gel column chromatography (solvent gradient: methanol/chloroform, 0.25% to 5.0%) to afford 2.73 g (53% yield, 5 steps) of (1S,2R)-2-(4-chlorobenzenesulfonylamino)-cyclohexanecarboxylic acid amide. An analytical sample was obtained after recrystallization from ethyl acetate/hexanes: $^1$H NMR (400 MHz, DMSO-d$_6$) 7.82 (d, 2 H, J=8.5), 7.64 (d, 2 H, J=8.6), 7.57 (d, 1 H, J=7.1), 7.22 (s, 1 H), 6.79 (s, 1 H), 3.43 (m, 1 H), 2.36 (m, 1 H), 1.72 (m, 2 H), 1.46 (m, 3 H), 1.17 (m, 3 H); MS m/e 339.1 (M+Na)$^+$. Anal. calcd. for C$_{13}$H$_{17}$ClN$_2$O$_3$S: C, 49.28; H, 5.40; N, 8.84. Found: C, 49.55; H, 5.24; N, 8.78. Optical rotation: [α]$_D$=−55.8 (c=6.78 mg/mL, DMF).

cis-2-(4-chlorobenzenesulfonylamino)-cyclohexanecarboxylic acid amide. To a solution of cis-2-aminocyclohexanecarboxylic acid amide (2.0 g, 14.0 mmol), and triethylamine (3.9 mL, 28 mmol) in dichloromethane (100 mL) was added 4-chlorobenzenesulfonyl chloride (2.95 g, 14.0 mmol). The resulting solution was stirred at room temperature for 18 h. The reaction was then diluted with dichloromethane (200 mL) and washed with $H_2O$, 1.0 M HCl, brine, and dried over $Na_2SO_4$. Further purification by flash chromatography (silica gel, 1% to 10% $MeOH/CHCl_3$) afforded cis-2-(4-chlorobenzenesulfonylamino)-cyclohexanecarboxylic acid amide (2.0 g) as a white solid in 45% yield over three steps: $^1H$ NMR (DMSO-$d_6$) δ 7.82 (m, 2 H), 7.63 (m, 2 H), 7.56 (d, 1 H, J=7.0 Hz), 7.22 (s br, 1 H), 6.80 (s br, 1 H), 3.43 (m, 1 H), 2.37 (m,1 H), 1.72 (m, 2 H), 1.45 (m, 3 H), 1.15 (m, 3 H); MS m/e 317.05 $(M+H)^+$.

trans-2-(4-chlorobenzenesulfonylamino)-cyclohexanecarboxylic acid amide. trans-2-Aminocyclohexanecarboxylic acid amide was converted to trans-2-(4-chlorobenzenesulfonylamino)-cyclohexanecarboxylic acid amide according to the method described for the preparation of cis-2-(4-chloro-benzenesulfonylamino)-cyclohexanecarboxylic acid amide. The product (200 mg) was isolated as a white solid in 10% yield over 3 steps: $^1H$ NMR ($CDCl_3$) δ 7.83 (d, 2 H, J=12.0 Hz), 7.47 (d, 2 H, J=8.0 Hz), 5.85 (m, 2 H), 5.70 (s br, 1 H), 3.31 (m, 1 H), 2.28 (m, 1 H), 1.96 (m, 1 H), 1.83 (m, 1 H), 1.57 (m, 3 H), 1.22 (m, 3 H); MS m/e 339.04 $(M+Na)^+$.

cis-exo-3-(4-chlorobenzenesulfonylamino)-bicyclo[2.2.1]heptane-2-carboxylic acid amide. cis-exo-3-Aminobicyclo[2.2.1]heptane-2-carboxylic acid amide (6.44 mmol) was converted to cis-exo-3-(4-chlorobenzenesulfonylamino)-bicyclo[2.2.1]heptane-2-carboxylic acid amide according to the method described for the preparation of cis-2-(4-chlorobenzenesulfonylamino)-cyclohexanecarboxylic acid amide. The product was isolated as a colorless oil and used in the next step without purification: $^1H$ NMR (400 MHz, DMSO-$d_6$) δ 7.82 (m, 2 H), 7.66 (m, 3 H), 7.27 (s br, 1 H), 6.89 (s br, 1 H), 3.36 (m, 2 H), 2.37 (m, 1 H), 2.14 (s br, 1 H), 1.90 (m, 1 H), 1.31 (m, 2 H), 1.02 (m, 3 H); MS m/e 351.01 $(M+Na)^+$.

cis-2-(4-chlorobenzenesulfonylamino)-cycloheptanecarboxylic acid amide. cis-2-Aminocycloheptanecarboxylic acid amide (2.20 g, 14.1 mmol) was converted to cis-2-(4-Chlorobenzenesulfonylamino)-cycloheptanecarboxylic acid amide according to the method described for the preparation of cis-2-(4-chlorobenzenesulfonylamino)-cyclohexanecarboxylic acid amide. The product (1.70 g) was isolated as a white solid in 37% yield: $^1H$ NMR (400 MHz, DMSO-$d_6$) δ 7.83 (d, 2 H, J=8.0 Hz), 7.64 (d, 2 H, J=8.0 Hz), 7.46 (d, 1 H, J=8.0 Hz), 7.18 (s, 1 H), 6.75 (s, 1 H), 3.43 (m, 1 H), 1.83–1.01 (m, 11 H); MS m/e 353.13 $(M+Na)^+$.

cis-2-(4-chlorobenzenesulfonylamino)-cyclopentanecarboxylic acid amide. cis-2-Aminocyclopentanecarboxylic acid amide (7.74 mmol) was converted to cis-2-(4-chlorobenzenesulfonylamino)-cyclopentanecarboxylic acid amide according to the method described for the preparation of cis-2-(4-chlorobenzenesulfonylamino)-cyclohexanecarboxylic acid amide. The product was isolated as white solid (2.0 g) in 80% yield and used in the next step without purification: $^1H$ NMR (400 MHz, DMSO-$d_6$) δ 7.82 (d, 2 H, J=12.0 Hz), 7.63 (m, 3 H), 7.26 (s br, 1 H), 6.89 (s br, 1 H), 3.62 (m, 1 H), 2.63 (m, 1 H), 1.70 (m, 3 H), 1.42 (m, 3 H); MS m/e 324.96 $(M+Na)^+$.

(1R,2S)-2-(4-Chlorobenzenesulfonylamino)-cyclohexanecarboxylic acid amide. (1R,2S)-2-(4-Chlorobenzenesulfonylamino)-cyclohexanecarboxylic acid (0.63 mmol) was dissolved in thionyl chloride (5 mL). The reaction was warmed to reflux for 30 minutes. The mixture was diluted with toluene (30 mL) then concentrated in vacuo. The residue was treated with dichloromethane (30 mL) and concentrated in vacuo. After dissolution in dichloromethane (10 mL), anhydrous ammonia gas was bubbled through the solution for 40 seconds causing a white precipitate to form. The reaction was stirred at room temperature for one hour. The reaction mixture was concentrated in vacuo. The residue was partitioned between ethyl acetate (20 mL) and water (15 mL). The organic layer was sequentially washed with water (1×10 mL) and brine (1×10 mL) then dried (magnesium sulfate), filtered and concentrated to a afford a yellow oil. The crude product (210 mg) was obtained in quantitative yield and used without further purification.: $^1H$ NMR (300 Mz, $CDCl_3$) δ 7.79 (d, 2 H, J=8.8), 7.46 (d, 2 H, J=8.4), 6.50 (d, 1 H, J=7.33), 6.62–6.52 (bd, 2 H), 3.32 (m, 1 H), 2.56 (m, 1 H), 1.98 (m, 1 H), 1.83 (m, 1 H), 1.70–1.45 (m, 4 H), 1.40–1.30 (m, 2 H); MS m/e 315 $(M-H)^-$.

(1S,$^2$S)-2-(4-Chlorobenzenesulfonylamino)-cyclohexanecarboxylic acid amide. (1S,2S)-2-(4-Chlorobenzenesulfonylamino)-cyclohexanecarboxylic acid amide was synthesized from (1S,2S)-2-(4-chlorobenzenesulfonylamino)-cyclohexanecarboxylic acid (0.76 mmol) according to the method described for the preparation of (1R,2S)-2-(4-chlorobenzenesulfonylamino)-cyclohexanecarboxylic acid amide. The crude product (230 mg) was obtained in 96% yield and carried into the next reaction without purification: $^1H$ NMR (300 Mz, $CDCl_3$) δ 7.72 (d, 2 H, J=8.4), 7.42 (d, 2 H, J=8.8), 3.23 (m, 1 H), 2.13 (m, 1 H), 1.85 (m, 1 H), 1.65 (m,3 H), 1.42 (m, 1 H), 1.13 (m, 3 H); MS m/e 339 $(M+Na)^+$.

(1R, 2R)-2-(4-Chlorobenzenesulfonylamino)-cyclohexanecarboxylic acid amide. (1R,2R)-2-(4-Chlorobenzenesulfonylamino)-cyclohexanecarboxylic acid amide was produced from (1R,2R)-2-(4-Chlorobenzenesulfonylamino)-cyclohexanecarboxylic acid according to the method described for the preparation of (1R,2S)-2-(4-chlorobenzenesulfonylamino)-cyclohexanecarboxylic acid amide. The crude product (230 mg) was obtained as a white solid in 96% yield. The product was carried on to the next reaction without purification.: $^1H$ NMR (300 Mz, $CDCl_3$) δ 7.72 (d, 2 H, J=8.4), 7.42 (d, 2 H, J=8.8), 3.23 (m, 1 H), 2.13 (m, 1 H), 1.85 (m, 1 ), 1.65 (m,3 H), 1.42 (m, 1 H), 1.13 (m, 3 H); MS m/e 315 $(M-H)^-$.

Intermediates of Formula 6

(1R, 2S)-2-[Benzyl (1-S-phenyl-ethyl)amino]cyclohexanecarboxylic acid methyl ester. 2.5 M n-Butyllithium in hexanes (7.25 mL, 18.1 mmol) was added dropwise to a cooled (ice water bath) mixture of S-(−)-N-benzyl-α-methylbenzylamine (15.1 mmol) in THF (60 mL). After stirring for 30 minutes the mixture was cooled to −95° C. (liquid nitrogen/acetone bath). A solution of methyl-1-cyclohexenecarboxylate (12.5 mmol) in THF (10 mL) was added to the chilled reaction mixture dropwise. After 1.5 hours the liquid nitrogen/acetone bath was replaced with a dry ice/acetone bath. The chilled reaction mixture was stirred for 2 hours and was quenched by the dropwise addition of 2,6-di-tert-butylphenol (25.2 mmol) in THF (20 mL). The reaction mixture was warmed to room temperature then concentrated in vacuo. The residue was dissolved in 100 mL of 50% dichloromethane in ether. The mixture was washed twice with brine. The organic layer was dried (magnesium sulfate), filtered and concentrated in vacuo. The crude material was purified by silica gel chromatography (solvent gradient: ethyl acetate/hexanes, 2% to 5%) to afford the desired product (2.25 g) as a yellow oil in 54% yield.: $^1$H NMR (300 Mz, CDCl$_3$) δ 7.38 (d, 4 H, J=7.3), 7.28 (m, 5 H), 7.18 (m, 2 H), 3.93 (m, 2 H), 3.77–3.68 (m, 1 H), 3.60 (s, 3 H), 2.68 (m, 1 H), 2.50 (m, 1 H), 2.14 (m, 1 H), 1.81 (m, 1 H), 1.70-1.52 (m, 4 H), 1.35-1.12 (m, 2 H) 1.27 (d, 3 H, J=7.0); MS m/e 352 (M+H)$^+$.

(1S,2S)-2-[Benzyl (1-S-phenyl-ethyl)amino]cyclohexanecarboxylic acid methyl ester. 0.5 M Potassium bis(trimethylsilyl)amide in toluene (22.8 mL, 11.4 mmol) was added dropwise to a solution of tert-butyl alcohol (1.65 mL, 17.3 mmol) in THF (40 mL). The reaction was stirred at room temperature for 30 minutes. A solution of (1R,2S)-2-[benzyl (1-S-phenyl-ethyl)amino]cyclohexanecarboxylic acid methyl ester (2.8 mmol) in THF (10 mL) was added to the reaction mixture dropwise. The reaction was stirred at ambient temperature overnight. Reaction mixture was concentrated in vacuo. Residue was dissolved in ether (50 ML) then washed with brine (2×25 mL). Organic layer was dried (magnesium sulfate), filtered then concentrated in vacuo. Residue was purified by silica gel chromatography (solvent gradient ethyl aceteate/hexanes, 2% to 5%) to afford the product as a clear colorless oil (615 mg) in 62% yield.: $^1$H NMR (300 Mz, CDCl$_3$) δ 7.35–7.17 (m, 10 H), 4.03 (q, 1 H, J=7.0), 3.82 (d, 1 H, J=14.3), 3.71 (d, 1 H, J=13.9), 3.00 (m, 1 H), 2.49 (m, 1 H), 1.96 (m, 1 H), 1.80 (m, 2 H), 1.65 (m, 1 H), 1.50–1.34 (m, 2 H), 1.41 (d, 3 H, J=7.0), 1.26–1.05 (m, 2 H); MS m/e 248 (M−C$_8$H$_8$+H)$^+$.

(1S,2R)-2-[Benzyl (1-R-phenyl-ethyl)amino]cyclohexanecarboxylic acid methyl ester. Methyl 1-cyclohexene-1-carboxylate (14.3 mmol) and R-(+)-N-benzyl-α-methylbenzylamine (21.5 mmol) were converted using a procedure analogous to the preparation of (1R,2S)-2-[benzyl (1-phenyl-ethyl)amino]cyclohexanecarboxylic acid methyl ester. Product (2.35 g) was obtained as a yellow oil in 47% yield.: $^1$H NMR (300 Mz, CDCl$_3$) δ 7.38 (d, 4 H, J=7.3), 7.28 (m, 5H), 7.18 (m, 2 H), 3.93 (m, 2 H), 3.77–3.68 (m, 1 H), 3.60 (s, 3 H), 2.68 (m, 1 H), 2.50 (m, 1 H), 2.14 (m, 1 H), 1.81 (m, 1 H), 1.70–1.52 (m, 4 H), 1.35–1.12 (m, 2 H) 1.27 (d, 3 H, J=7.0); MS m/e 352 (M+H)$^+$.

(1R,2R)-2-[Benzyl (1-R-phenyl-ethyl)amino]cyclohexanecarboxylic acid methyl ester. (1S,2R)-2-[Benzyl (1-R-phenyl-ethyl)amino]cyclohexanecarboxylic acid methyl ester (1.7 mmol) was converted to (1R,2R)-2-[Benzyl (1-R-phenyl-ethyl) amino]cyclohexanecarboxylic acid methyl ester according to the method described for the preparation of (1S,2S)-2-[Benzyl (1-R-phenyl-ethyl)amino]cyclohexanecarboxylic acid methyl ester. The product was obtained as a clear oil in 54% yield.: $^1$H NMR (300 Mz, CDCl$_3$) δ 7.35–7.17 (m, 10 H), 4.03 (q, 1 H, J=7.0), 3.82 (d, 1 H, J=14.3), 3.71 (d, 1 H, J=13.9), 3.00 (m, 1 H), 2.49 (m, 1 H), 1.96 (m, 1 H), 1.80 (m, 2 H), 1.65 (m, 1 H), 1.50-1.34 (m, 2 H), 1.41 (d, 3 H, J=7.0), 1.26–1.05 (m, 2 H); MS m/e 352 (M+H)$^+$.

Intermediates of Formula 7

(1R, 2S)-2-(4-Chlorobenzenesulfonylamino)-cyclohexanecarboxylic acid methyl ester. A catalytic amount of 5% palladium on carbon was added to a solution of (1R,2S)-2-[benzyl (1-S-phenyl-ethyl)amino]cyclohexanecarboxylic acid methyl ester (1.1 mmol) in acetic acid (10 mL). Reaction vessel was placed on a Parr apparatus and charged with 50 psi of hydrogen gas. Reaction was shaken at room temperature overnight. Reaction mixture was filtered over celite. Filtrate was concentrated. Residue was treated with toluene (30 mL) then concentrated in vacuo. Residue was treated with acetonitrile (30 mL) then concentrated in vacuo. Residue was partitioned between THF (15 mL) and saturated aqueous sodium bicarbonate solution (30 mL). 4-Chlorobenzenesulfonyl chloride (1.5 mmol) was added to the mixture. Reaction was stirred vigorously overnight at ambient temperature. Reaction mixture was extracted twice with ethyl acetate (30 mL). Combined extracts were sequentially washed with 1 N sodium hydroxide (1×30 mL), 1 N hydrochloric acid (2×30 mL), and brine (1×30 mL). The organic layer was dried (magnesium sulfate), filtered and concentrated in vacuo. The crude product (275 mg) was obtained as a yellow oil in 73% yield. Product was carried on to the next reaction without purification.: $^1$H NMR (300 Mz, CDCl$_3$) δ 7.76 (d, 2 H, J=8.8), 7.47 (d, 2 H, J=8.8), 5.59 (d, 1 H, J=8.8), 3.57 (s, 3 H), 3.43 (m, 1 H), 2.65 (m, 1 H), 1.97 (m, 1 H), 1.83–1.68 (m, 2 H), 1.65–1.56 (m, 1 H), 1.54–1.43 (m, 2 H), 1.32–1.17 (m, 2 H).

(1S, 2S)-2-(4-Chlorobenzenesulfonylamino)-cyclohexanecarboxylic acid methyl ester. A catalytic amount of 5% palladium on carbon was added to a solution of (1S,2S)-2-[Benzyl (1-S-phenyl-ethyl)amino]cyclohexanecarboxylic acid methyl ester (1.7 mmol) in acetic acid (20 mL). Reaction vessel was placed on a Parr hydrogenation apparatus and charged with 50 psi of hydrogen gas. Reaction was shaken at room temperature overnight. Reaction mixture was filtered over celite. Filtrate was concentrated in vacuo. Residue was treated with toluene (30 mL) then concentrated in vacuo. Residue was treated with acetonitrile (30 mL) then concentrated in vacuo. Residue was partitioned between 1,4-dioxane (15 mL) and saturated aqueous sodium bicarbonate solution (10 mL). 4-Chlorobenzenesulfonyl chloride (2.2 mmol) was added to the reaction mixture with vigorous stirring. Reaction was stirred at room temperature for 5 hours. 1 N Sodium hydroxide (10 mL) was added to the mixture. Mixture was extracted with ethyl acetate (2×20 mL). Combined extracts were washed sequentially with 1 N sodium hydroxide (20 mL), 1 N hydrochloric acid (2×20 mL) and brine (1×15 mL). Organic layer was dryed (magnesium sulfate), filtered and concentrated in vacuo. Crude product was obtained as a yellow oil in 63% yield. Material was used without purification.: $^1$H NMR (300 Mz, CDCl$_3$) δ 7.75 (d, 2 H, J=8.8), 7.47 (d, 2 H, J=8.8), 4.71 (d, 1 H, J=8.1), 3.42 (s, 3 H), 2.22 (m, 1 H,), 2.05 (m, 1 H), 1.86 (m, 2 H), 1.67 (m, 2 H) 1.64–1.49 (m, 1 H), 1.30–1.10 (m, 3 H).

(1R,2R)-2-(4-Chlorobenzenesulfonylamino)-cyclohexanecarboxylic acid methyl ester. (1R,2R)-2-[Benzyl (1-R-phenyl-ethyl)amino]cyclohexanecarboxylic acid methyl ester (0.88 mmol) was converted to (1R,2R)-2-(4-Chlorobenzenesulfonylamino)-cyclohexanecarboxylic acid methyl ester according to the method described for the preparation of (1S,2S)-2-(4-Chlorobenzenesulfonylamino)-cyclohexanecarboxylic acid methyl ester. Product was obtained as a yellow oil in 67% yield. Material was used without purification.: $^1$H NMR (300 Mz, CDCl$_3$) δ 7.75 (d, 2 H, J=8.8), 7.47 (d, 2 H, J=8.8), 4.71 (d, 1 H), J=8.1), 3.42 (s, 3 H), 2.22 (m, 1 H,), 2.05 (m, 1 H), 1.86 (m, 2 H), 1.67 (m, 2 H) 1.64–1.49 (m, 1 H), 1.30–1.10 (m, 3 H); MS m/e 330 (M−H)$^-$.

Intermediates of Formula 8

(1R, 2S)-2-(4-Chlorobenzenesulfonylamino)-cyclohexanecarboxylic acid. Lithium hydroxide monohydrate (1.7 mmol) was added to a mixture of (1R,2S)-2-(4-chlorobenzenesulfonylamino)-cyclohexanecarboxylic acid methyl ester in THF (8 mL), methanol (8mL) and water (8 mL). Reaction stirred at room temperature overnight. Organic solvents were removed from the mixture in vacuo. Remaining aqueous was washed with ether (2×15 mL). Aqueous layer was made acidic to litmus paper with 1 N hydrochloric acid. Mixture was extracted with ethyl acetate (2×20 mL). Combined extracts were washed with brine (1×10 mL) then dried (magnesium sulfate), filtered and concentrated in vacuo. The product (208 mg) was obtained as a white solid in 80% yield: $^1$H NMR (300 Mz, CDCl$_3$) δ 7.70 (d, 2 H, J=8.8), 7.48 (d, 4 H, J=8.8), 6.20 (d, 1 H, J=9.5), 3.41 (m, 1 H), 2.81 (dd, 1 H, J$_d$=4.4, J$_d$=4.8), 2.03 (m, 1 H), 1.80 (m, 1 H), 1.62 (m, 1 H), 1.44 (m, 2 H), 1.25 (m, 2 H); MS m/e 316 (M−H)$^-$.

(1S,2S)-2-(4-Chlorobenzenesulfonylamino)-cyclohexanecarboxylic acid. Lithium hydroxide monohydrate (2.3 mmol) was added to a solution of (1S,2S)-2-(4-Chlorobenzenesulfonylamino)-cyclohexanecarboxylic acid (1.1 mmol) in methanol (10 mL), THF (10 mL) and water (10 mL). Reaction was stirred at room temperature overnight. Reaction mixture was then warmed to 50° C. for 5 hours. Organic solvents were removed from the reaction mixture in vacuo. Remaining aqueous was washed with ether (2×10 mL) then made acidic to litmus with 1 N hydrochloric acid. Mixture was extracted with ethyl acetate (2×15 mL). Combined extracts were washed with brine (1×10 mL) then dried (magnesium sulfate), filtered and concentrated in vacuo to yield the crude product (245 mg) as a white solid in 73% yield. Material was used in the next reaction without further purification.: $^1$H NMR (300 Mz, CDCl$_3$) δ 7.77 (d, 2 H, J=8.8), 7.45 (d, 2 H, J=8.4), 4.99 (d, 1 H, J=8.4), 3.35 (m, 1 H), 2.26 (m, 1 H), 2.01 (m, 2 H), 1.67 (m, 2 H), 1.50 (m, 1 H), 1.31-1.11 (m, 3 H); MS m/e 316 (M−H)$^-$.

(1R, 2R)-2-(4-Chlorobenzenesulfonylamino)-cyclohexanecarboxylic acid. (1R,2R)-2-(4-Chlorobenzenesulfonylamino)-cyclohexanecarboxylic acid methyl ester (0.57 mmol) was converted to (1R,2R)-2-(4-Chlorobenzenesulfonylamino)-cyclohexanecarboxylic acid according to the method described for the preparation of (1S,2S)-2-(4-Chlorobenzenesulfonylamino)-cyclohexanecarboxylic acid. Product was obtained as a white solid in 81% yield. Material was carried forward without purification.: $^1$H NMR (300 Mz, CDCl$_3$) δ 7.77 (d, 2 H, J=8.8), 7.45 (d, 2 H, J=8.4), 4.99 (d, 1 H, J=8.4), 3.35 (m, 1 H), 2.26 (m, 1 H), 2.01 (m, 2 H), 1.67 (m, 2 H), 1.50 (m, 1 H), 1.31–1.11 (m, 3 H); MS m/e 316 (M−H)$^-$.

EXAMPLE 1

4-[[(1R,2S)-(2-Carbamoyl-cyclohexyl)-(4-chlorobenzenesulfonyl)-amino]-methyl]-benzoic acid methyl ester. A mixture of (1S,2R)-2-(4-chlorobenzenesulfonylamino)-cyclohexanecarboxylic acid amide (670 mg, 2.12 mmol), methyl 4-(bromomethyl)benzoate (534 mg, 2.33 mmol), cesium carbonate (1.04 g, 3.18 mmol) and acetonitrile (20 mL) was stirred vigorously at room temperature for 18 h. The crude mixture was filtered through celite and concentrated in vacuo. The product was purified by silica gel column chromatography (methanol/chloroform, 0.25%) to afford 213 mg (22% yield) of 4-[[(1R,2S)-(2-carbamoyl-cyclohexyl)-(4-chlorobenzenesulfonyl)-amino]-methyl]-benzoic acid methyl ester. An analytical sample was obtained after recrystallization from ethyl acetate/hexanes: $^1$H NMR (400 Mz, DMSO) δ 7.85 (d, 2 H, J=8.3), 7.82 (d, 2 H, J=8.5), 7.63 (d, 2 H, J=8.5), 7.42 (d, 2 H, J=8.3), 7.28 (br s, 1 H), 6.60 (br, s, 1 H), 4.64 (ABq, 2 H, Δv=69.4, J$_{ab}$=17.4), 3.88 (m, 1 H), 3.85 (s, 3 H), 2.79 (m, 1 H), 2.42 (m, 1 H), 1.64 (m, 2 H), 1.38–1.21 (m, 3 H), 0.90 (m, 1 H); MS m/e 465.1 (M+H)$^+$.

EXAMPLE 2

4-[[(1R,2S)-(2-Carbamoyl-cyclohexyl)-(4-chlorobenzenesulfonyl)-amino]-methyl]-N-ethyl-benzamide. A mixture of 4-[[(1R,2S)-(2-carbamoyl-cyclohexyl)-(4-chlorobenzenesulfonyl)-amino]-methyl]-benzoic acid methyl ester (50 mg, 0.108 mmol, Example 1) and ethylamine (2.0 M solution in methanol, 5 mL) was left to stir at room temperature for 10 days. The mixture was concentrated in vacuo. The product was purified by silica gel column chromatography (methanol/chloroform, 0.25%) to afford 19 mg (37% yield) of the titled compound: $^1$H NMR (500 Mz, DMSO) δ 8.39 (t, 1 H, J=5.5), 7.80 (d, 2 H, J=8.5), 7.72 (d, 2 H, J=8.2), 7.63 (d, 2 H, J=8.6), 7.33 (d, 2 H, J=8.2), 7.31 (br s, 1 H), 6.65 (br, s, 1 H), 4.61 (ABq, 2 H, Δv=100, J$_{ab}$=17.1), 3.87 (dt, 1 H, J$_d$=12.5, J$_t$=4.0), 3.28 (m, 2 H), 2.79 (m, 1 H), 2.41 (m, 1 H), 1.78 (m, 1 H), 1.63 (m, 2 H), 1.39–1.20 (m, 3 H), 1.12 (t, 3 H, J=7.3), 0.92 (m, 1 H); MS m/e 478.1 (M+H)$^+$.

EXAMPLE 3

(1S,2R)-2-[(4-tert-Butyl-benzyl)-(4-chlorobenzenesulfonyl)-amino]-cyclohexanecarboxylic acid amide. The titled compound was prepared in 69% yield from (1S,2R)-2-(4-chlorobenzenesulfonylamino)-cyclohexanecarboxylic acid amide (75 mg, 0.237 mmol) and 1-bromomethyl-4-tert-butyl-benzene (57 mg, 0.249 mmol) according to the procedure described for Example 3: $^1$H NMR (500 Mz, DMSO) δ 7.58 (d, 2 H, J=8.9), 7.48 (d, 2 H, J=8.6), 7.38 (br s, 1 H), 7.18 (d, 2 H, J=8.2), 7.09 (d, 2 H, J=8.2), 6.76 (br, s, 1 H), 4.53 (ABq, 2 H, Δv=39.4, J$_{ab}$=16.2), 3. 95 (dt, 1 H, J$_d$=12.8, J$_t$=4.0), 2.80 (m, 1 H), 1.79 (m, 1 H), 1.72 (m, 1 H), 1.63 (m, 1 H), 1.48 (m, 2 H), 1.33 (m, 2 H), 1.25 (s, 9 H), 1.18 (m, 2 H); MS m/e 485.3 (M+Na)$^+$.

EXAMPLE 4

(1S,2R)-2-[(4-Chlorobenzenesulfonyl)-(3-chloro-4-trifluoromethoxy-benzyl)-amino]-cyclohexanecarboxylic acid amide. The titled compound was prepared in 59% yield from (1S,2R)-2-(4-chlorobenzenesulfonylamino)-cyclohexanecarboxylic acid amide (75 mg, 0.237 mmol) and 4-bromomethyl-2-chloro-1-trifluoromethoxy-benzene (72 mg, 0.249 mmol) according to the procedure described for Example 3: $^1$H NMR (500 Mz, DMSO) δ 7.81 (d, 2 H, J=8.5), 7.63 (d, 2 H, J=8.6), 7.48 (br s, 1 H), 7.44–7.35 (m, 4 H), 6.70 (br s, 1 H), 4.56 (ABq, 2 H, Δv=106, J$_{ab}$=17.1), 3.88 (m, 1 H), 2.82 (m, 1 H), 2.44 (m, 1 H), 1.80 (m, 1 H), 1.67 (m, 2 H), 1.39–1.22 (m, 3 H), 0.89 (m, 1 H); MS m/e 547.2 (M+Na)$^+$.

EXAMPLE 5

(1S,2R)-2-[(4-Chlorobenzenesulfonyl)-(3-chloro-4fluoro-benzyl)-amino]-cyclohexanecarboxylic acid amide. The titled compound was prepared in 43% yield from (1S,2R)-2-(4-chlorobenzenesulfonylamino)-cyclohexanecarboxylic acid amide (75 mg, 0.237 mmol) and 4-bromomethyl-2-chloro-1-fluoro-benzene (56 mg, 0.249 mmol) according to the procedure described for Example 3: $^1$H NMR (500 Mz, DMSO) δ 7.80 (d, 2 H, J=8.5), 7.63 (d, 2 H, J=8.8), 7.38–7.27 (m, 4 H), 6.67 (br s, 1 H), 4.52 (ABq, 2 H, Δv=92.1, J$_{ab}$=17.1), 3.87, 2.79 (m, 1 H), 2.44 (m, 1 H), 1.78 (m, 1 H), 1.64 (m, 2 H), 1.42–1.20 (m, 3 H), 0.90 (m, 1 H); MS m/e 481.2 (M+Na)$^+$.

EXAMPLE 6

(1S,2R)-2-[(4- Chlorobenzenesulfonyl)-[4-( -hydroxy-1-methyl-ethyl)-benzyl]-amino]-cyclohexanecarboxylic acid amide. Ethylmagnesium bromide (1.4 M/THF, 0.77 mL, 1.08 mmol) was added to a solution of 4-[[((1R,2S)-2-carbamoyl-cyclohexyl)-(4-chlorobenzenesulfonyl)-amino]-methyl]-benzoic acid methyl ester (50 mg, 0.108 mmol, Example 1) in THF at 0° C. The resulting mixture was allowed to warm to room temperature and left to stir for 24 h. The reaction was quenched with 1 N HCl (50 mL) and the aqueous was extracted with ethyl acetate (3×100 mL). The organic layer was dried (magnesium sulfate), filtered, and concentrated in vacuo. The crude material was purified by silica gel column chromatography (methanol/chloroform, 0.25%) to afford 22.7 mg (45% yield) of the titled compound: $^1$H NMR (400 Mz, CDCl$_3$) δ 7.52 (d, 2 H, J=8.8), 7.33 (m, 4 H), 7.20 (d, 2 H, J=8.1), 4.72 (ABq, 2 H, Δv=23.2, J$_{ab}$=16.4), 4.02 (dt, 1 H, J$_d$=12.7, J=3.4), 3.15 (m, 1 H), 2.00 (m, 1 H), 1.88–1.75 (m, 3 H), 1.65 (m, 4 H), 1.54 (s, 6 H), 1.50 (m, 1 H), 1.35 (m, 1 H); MS m/e 469.3 (M–H$_2$O+Na)$^+$.

EXAMPLE 7

(1S,2R)-2-[(4-Chlorobenzenesulfonyl)-(5-chloro-thiophen-2-ylmethyl)-amino]-cyclohexanecarboxylic acid amide. The titled compound was prepared in 38% yield from (1S,2R)-2-(4-chlorobenzenesulfonylamino)-cyclohexanecarboxylic acid amide (75 mg, 0.237 mmol) and 2-bromomethyl-5-chloro-thiophene (83 mg, 0.498 mmol) according to the procedure described in Example 3: $^1$H NMR (400 Mz, CDCl$_3$) δ 7.72 (d, 2 H, J=6.6), 7.59 (d, 2 H, J=8.9), 7.39 (br s, 1 H), 6.88 (d, 1 H, J=3.7), 6.79 (br s, 1 H), 4.69 (s, 2 H), 3.83 (dt, 1 H, J$_d$=12.7, J=3.7), 2.71 (m, 1 H), 2.52 (m, 1 H), 1.79–1.69 (m, 2 H), 1.61 (m, 1 H), 1.49–1.22 (m, 3 H), 1.11 (m, 1 H); MS m/e 469.1 (M+Na)$^+$.

EXAMPLE 8

(1S,2R)-2-[(4-Chlorobenzenesulfonyl)-(4-trifluoromethylsulfanyl-benzyl)-amino]-cyclohexanecarboxylic acid amide. The titled compound was prepared in 64% yield from (1S,2R)-2-(4-chlorobenzenesulfonylamino)-cyclohexanecarboxylic acid amide (100 mg, 0.316 mmol) and 1-bromomethyl-4-trifluoromethylsulfanyl-benzene (90 mg, 0.332 mmol) according to the procedure described in Example 3: $^1$H NMR (400 Mz, DMSO-d6) δ 7.79 (d, 2 H, J=8.8), 7.61 (d, 2 H, J=8.8), 7.59 (d, 2 H), J=8.1), 7.43 (d, 2 H, J=8.1), 7.32 (br s, 1 H), 6.65 (br s, 1 H), 4.62 (ABq, 2 H, Δv=73.1, J$_{ab}$=17.3), 3.88 (dt, 1 H, J$_d$=12.7, J$_f$=3.9), 2.79 (m, 1 H), 2.43 (m, 1 H), 1.79 (m, 1 H), 1.65 (m, 2 H), 1.42–1.19 (m, 3 H), 0.94 (m, 1 H); MS m/e 529.1 (M+Na)$^+$. Optical rotation: [α]$_D$=−28.6 (c=5.87 mg/mL, MeOH).

EXAMPLE 9 cis-2-[(4-Chlorobenzenesulfonyl)-(4-trifluoromethoxy-benzyl)-amino]-cyclohexanecarboxylic acid amide. cis-2-(4-Chloro-benzenesulfonylamino)-cyclohexanecarboxylic acid amide (200 mg, 0.63 mmol), CsCO$_3$ (250 mg, 0.76 mmol), and 1-bromomethyl-4-trifluormethoxy-benzene (155 mg, 0.69 mmol) was stirred in acetonitrile (15 mL) at room temperature for 18 h. The reaction was then diluted with EtOAc (150 mL) and washed with H$_2$O, brine, dried over Na$_2$SO$_4$ and concentrated to give a crude white wax. Further purification by flash chromatography (silica gel, 0.5%–1% MeOH/CHCl$_3$) afforded the titled compound (205 mg) as a white solid in 67% yield: $^1$H NMR (DMSO-d$_6$) δ 7.75 (d, 2 H, J=8.0 Hz), 7.59 (d, 2 H, J=8.0 Hz), 7.36 (m, 3 H), 7.21 (d, 2 H, J=8.0 Hz), 6.69 (s br, 1 H), 4.58 (AB$_2$, 2 H, Δv=17, J$_{ab}$=64 Hz), 3.89 (m, 1 H), 2.79 (s, 1 H), 2.44 (m, 1 H), 1.78 (m, 1 H), 1.66 (m, 2 H), 1.31 (m, 3 H), 0.98 (m, 1 H); MS m/e 491.03 (M+H)$^+$.

EXAMPLE 10 cis-2-[(4-Chlorobenzenesulfonyl)-(4-trifluoromethyl-benzyl)-amino]-cyclohexanecarboxylic acid amide. The titled compound (155 mg) was prepared in 52% yield from cis-2-(4-chlorobenzenesulfonylamino)-cyclohexanecarboxylic acid amide and 1-bromomethyl-4-trifluoromethyl-benzene according to the procedure described in Example 11: $^1$H NMR (DMSO-d$_6$) δ 7.80 (d, 2 H, J=8.6 Hz), 7.61 (m, 4 H), 7.49 (d, 2 H, J=8.0 Hz), 7.32 (s, 1 H), 6.66 (s, 1 H), 4.65 (AB$_2$, 2 H, Δv=17, J$_{ab}$=64 Hz), 3.88 (m, 1 H), 2.80 (s, 1 H), 2.44 (m, 1 H), 1.79 (m, 1 H), 1.65 (m, 2 H), 1.30 (m, 3 H), 0.92 (m, 1 H); MS m/e 475.01 (M+H)$^+$.

EXAMPLE 11 cis-2-[(4-Chlorobenzenesulfonyl)-(4-fluoro-benzyl)-amino]-cyclohexanecarboxylic acid amide. The titled compound (178 mg) was prepared in 67% yield from cis-2-(4-chlorobenzenesulfonylamino)-cyclohexanecarboxylic acid amide and 1-bromomethyl-4-fluoro-benzene according to the procedure described in Example 11: $^1$H NMR (DMSO-d$_6$) δ 7.74 (d, 2 H, J=8.0 Hz), 7.60 (d, 2 H, J=8.0 Hz), 7.28 (m, 3 H), 7.05 (m, 2 H), 6.67 (s, 1 H), 4.54 (AB$_2$, 2 H, Δv=17, J$_{ab}$=57 Hz), 3.87 (m, 1 H), 2.76 (m, 1 H), 2.45 (m, 1 H), 1.47 (m, 6 H), 0.97 (m, 1 H); MS m/e 425.02 (M+H)$^+$.

EXAMPLE 12 cis-2-[(4-Chlorobenzenesulfonyl)-(4-cyano-benzyl)-amino]-cyclohexanecarboxylic acid amide. The titled compound (133 mg) was prepared in 49% yield from cis-2-(4-chlorobenzenesulfonylamino)-cyclohexanecarboxylic acid amide and 4-bromomethyl-benzonitrile according to the procedure described in Example 11: $^1$H NMR (DMSO-d$_6$) δ 7.84 (d, 2 H, J=8.0 Hz), 7.73 (d, 2 H, J=8.0 Hz), 7.66 (d, 2 H,J=8.0 Hz), 7.48 (d, 2 H,J=8.0 Hz), 7.29 (s, 1 H), 6.60 (s, 1 H), 4.63 (AB$_2$,2 H,Δv=16,J$_{ab}$=76 Hz), 3.84 (m, 1 H), 2.79 (m, 1 H), 2.41 (m, 1 H), 1.64 (m, 2 H), 1.27 (m, 3 H), 0.85 (m, 1 H); MS m/e 454.02 (M+Na)$^+$.

EXAMPLE 13 cis-4-[[(2-Carbamoyl-cyclohexyl)-(4-chlorobenzene-sulfonyl)-amino]-methyl]-benzoic acid methyl ester. The titled compound (90 mg) was prepared in 61% yield from cis-2-(4-chlorobenzenesulfonylamino)-cyclohexanecarboxylic acid amide and methyl 4-(bromomethyl)benzoate according to the procedure described in Example 11: $^1$H NMR (DMSO-d$_6$) δ 7.83 (m, 4 H), 7.64 (d, 2 H, J=8.0 Hz), 7.42 (d, 2 H,J=8.0 Hz), 7.28 (s, 1 H), 6.61 (s, 1 H), 4.64 (AB$_2$,2 H,Δv=20,J$_{ab}$=72 Hz), 3.85 (m, 4 H), 2.79 (m, 1 H), 2.42 (m, 1 H), 1.78 (m, 1 H), 1.63 (m, 2 H), 1.28 (m, 3 H), 0.90 (m, 1 H); MS m/e 464.98 (M+H)$^+$.

EXAMPLE 14 trans-2-[(4-Chlorobenzenesulfonyl)-(4-trifluoromethoxy-benzyl)-amino]-cyclohexanecarboxylic acid amide. The titled compound was prepared in 20% yield from trans-2-

(4-chlorobenzenesulfonylamino)-cyclohexanecarboxylic acid amide and 1-bromomethyl-4-trifluoromethoxy-benzene according to the procedure described in Example 11: $^1$H NMR (DMSO-d$_6$) δ 7.63 (d, 2 H, J=8.0 Hz), 7.43 (m, 4 H), 7.37 (s br, 1 H), 7.18 (d, 2 H, J=8.0 Hz), 6.81 (s br, 1 H), 4.36 (AB$_2$, 2 H,Δv=12,J$_{ab}$=72 Hz), 4.01 (s br, 1 H), 1.83 (m, 1 H), 1.30 (m, 8 H); MS m/e 490.97 (M+H)$^+$.

EXAMPLE 15 trans-2-[(4- Chlorobenzenesulfonyl)-(4-trifluoromethyl-benzyl)-amino]-cyclohexanecarboxylic acid amide. The titled compound (34 mg) was prepared in 45% yield from trans-2-(4-chlorobenzenesulfonylamino)-cyclohexanecarboxylic acid amide and 1-bromomethyl-4-trifluoromethyl-benzene according to the N-alkylation procedure described in Example 11: $^1$H NMR (DMSO-d$_6$) δ 7.77 (d, 2 H, J=8.0 Hz), 7.65 (d, 2 H, J=8.0 Hz), 7.57 (m, 3 H), 7.45 (d, 2 H, J=12.0 Hz), 7.35 (s, 1 H), 6.80 (s, 1H), 4.44 (AB$_2$,2 H,ΔV=16,J$_{ab}$=84 Hz), 4.01 (m, 1 H), 1.39 (m, 8 H); MS m/e 475.04 (M+H)$^+$.

EXAMPLE 16 trans-2-[(4- Chlorobenzenesulfonyl)-(4-cyano-benzyl)-amino]-cyclohexanecarboxylic acid amide. The titled compound was prepared in 43% yield from trans-2-(4-chlorobenzenesulfonylamino)-cyclohexanecarboxylic acid amide and 4-bromomethyl-benzonitrile according to the procedure described in Example 11: $^1$H NMR (DMSO-d$_6$) δ 7.71(m, 4 H), 7.53 (m, 4 H), 7.29 (s, 1 H), 6.76 (s, 1 H), 4.44 (AB$_2$,2 H,Δv=16,J$_{ab}$=84 Hz), 3.96 (m, 1 H), 1.80 (m, 1 H), 1.57 (m, 3 H), 1.17 (m, 5 H); MS m/e 432.01 (M+H)$^+$.

EXAMPLE 17 cis-exo-3-[(4-Chlorobenzenesulfonyl)-(4-trifluoromethyl-benzyl)-amino]-bicyclo[2.2.1]heptane-2-carboxylic acid amide. The titled compound (205 mg) was prepared in 55% yield from cis-exo-3-(4-chlorobenzenesulfonylamino)-bicyclo[2.2.1]heptane-2-carboxylic acid amide (250 mg, 0.76 mmol) and 1-bromomethyl-4-trifluoromethyl-benzene according to the N-alkylation procedure described in Example 11: $^1$H NMR (DMSO-d$_6$) δ 7.67 (d, 2 H, J=8.0 Hz), 7.55 (m, 4 H), 7.41 (d, 2 H, J=8.0 Hz), 7.02 (s br, 1 H), 6.71 (s br, 1 H), 4.63 (AB$_2$,2 H,Δv=20,J$_{ab}$=60 Hz), 4.16 (d, 1 H, J=8.0 Hz), 2.66 (d, 1 H, J=12.0 Hz), 2.19 (m, 2 H), 1.91 (m, 1 H), 1.46–0.97 (m, 5 H); MS m/e 486.97 (M+H)$^+$.

EXAMPLE 18 cis-exo-3-[(4-Chlorobenzenesulfonyl)-(4-cyano-benzyl)-amino]-bicyclo[2.2.1]heptane-2-carboxylic acid amide. The titled compound (78 mg) was prepared in 23% yield from cis-exo-3-(4-chlorobenzenesulfonylamino)-bicyclo[2.2.1]heptane-2-carboxylic acid amide (250 mg, 0.76 mmol) and 4-bromomethyl-benzonitrile according to the N-alkylation procedure described in Example 11: $^1$H NMR (DMSO-d$_6$) δ 7.70 (m, 4 H), 7.58 (d, 2 H, J=8.0 Hz), 7.41 (d, 2 H, J=8.0 Hz), 7.01 (s br, 1 H), 6.68 (s br, 1 H), 4.61 (AB$_2$,2 H,Δv=16,J$_{ab}$=64 Hz), 4.12 (d, 1 H, J=8.0 Hz), 2.64 (d, 1 H, J=8.0 Hz), 2.16 (m, 2 H), 1.83 (s, 1 H), 1.41 (m, 2 H), 1.15 (m, 2 H), 1.00 (d, 1 H, J=8.0 Hz); MS m/e465.95 (M+Na)$^+$.

EXAMPLE 19 cis-exo-4-[[(3-Carbamoyl-bicyclo[2.2.1]hept-2-yl)-(4-chlorobenzenesulfonyl)-amino]-methyl]-benzoic acid methyl ester. The titled compound (30 mg) was prepared in 8% yield from cis-exo-3-(4-chlorobenzenesulfonylamino)-bicyclo[2.2.1]heptane-2-carboxylic acid amide (250 mg, 0.76 mmol) and methyl 4-(bromomethyl)benzoate according to the N-alkylation procedure described in Example 11: $^1$H NMR (DMSO-d$_6$) δ 7.81 (d, 2 H, J=8.0 Hz), 7.69 (d, 2 H, J=8.0 Hz), 7.56 (d, 2 H, J=8.0 Hz), 7.33 (d, 2 H, J=8.0 Hz), 6.96 (s br, 1 H), 6.69 (s br, 1 H), 4.64 (AB$_2$,2 H,Δv=20,J$_{ab}$=56 Hz), 4.14 (d, 1 H, J=8.0 Hz), 3.84 (s, 3 H), 2.64 (d, 1 H, J=8.0 Hz), 2.17 (m, 2 H), 1.89 (s, 1 H), 1.40 (m, 2 H), 1.16 (m, 2 H) 0.99 (d, 1 H, J=12.0 Hz); MS m/e 476.98 (M+H)$^+$.

EXAMPLE 20 cis-4-[[(2-Carbamoyl-cycloheptyl)-(4-chlorobenzenesulfonyl)-amino]-methyl]-benzoic acid methyl ester. The titled compound (321 mg) was prepared in 28% yield from cis-2-(4-chlorobenzenesulfonylamino)-cycloheptanecarboxylic acid amide (800 mg, 2.42 mmol) and methyl 4-(bromomethyl)benzoate according to the N-alkylation procedure described in Example 11: $^1$H NMR (DMSO-d$_6$) δ 7.83 (m, 4 H), 7.65 (d, 2 H,J=8.0 Hz), 7.45 (d, 2 H, J=12.0 Hz), 7.31 (s br, 1 H), 6.64 (s br, 1 H), 4.60 (AB$_2$,2 H,Δv=16,J$_{ab}$=92 Hz), 3.96 (m, 1 H), 3.85 (m, 3 H), 2.78 (m, 1 H), 2.28 (m, 1 H), 1.72 (m, 2 H), 1.35 (m, 7 H); MS m/e 479.12 (M+H)$^+$.

EXAMPLE 21 cis-2-[(4-Chlorobenzenesulfonyl)-(4-cyano-benzyl)-amino]-cycloheptanecarboxylic acid amide. The titled compound (6.4 mg) was prepared in 3% yield from cis-2-(4-chlorobenzenesulfonylamino)-cycloheptanecarboxylic acid amide (150 mg, 0.45 mmol) and 4-bromomethyl-benzonitrile according to the N-alkylation procedure described in Example 11: $^1$H NMR (DMSO-d$_6$) δ 7.84 (m, 3 H), 7.69 (m, 4 H), 7.50 (d, 1 H, J=8.0 Hz), 7.31 (s br, 1 H), 6.65 (s br, 1 H), 4.60 (AB$_2$,2 H,Δv=16,J$_{ab}$=96 Hz), 3.93 (m, 1 H), 2.79 (m, 1 H), 2.24 (m, 1 H), 1.72 (m, 2 H), 1.31 (m, 7 H).

EXAMPLE 22 cis-2-[(4-Chlorobenzenesulfonyl)-(4-trifluoromethyl-benzyl)-amino]-cycloheptanecarboxylic acid amide. The titled compound (127 mg) was prepared in 58% yield from cis-2-(4-chlorobenzenesulfonylamino)-cycloheptanecarboxylic acid amide (150 mg, 0.45 mmol) and 1-bromomethyl-4-trifluoromethyl-benzene according to the N-alkylation procedure described in Example 11: $^1$H NMR (DMSO-d$_6$) δ 7.80 (m, 2 H, J=8.0 Hz), 7.62 (m, 4 H), 7.52 (d, 2 H, J=8.0 Hz), 7.35 (s br, 1 H), 6.70 (s br, 1 H), 4.61 (AB$_2$,2 H,Δv=20,J$_{ab}$=104 Hz), 3.98 (m, 1 H), 2.80 (m, 1 H), 2.29 (m, 1 H), 1.74 (m, 2 H), 1.43 (m, 5 H), 1.22 (m, 2 H); MS m/e 511.05 (M+Na)$^+$.

EXAMPLE 23 cis-2-[(4-Chlorobenzenesulfonyl)-(4-pyrazol-1-yl-benzyl)-amino]-cycloheptanecarboxylic acid amide. The titled compound (40 mg) was prepared in 18% yield from cis-2-(4-chlorobenzenesulfonylamino)-cycloheptanecarboxylic acid amide (150 mg, 0.45 mmol) and 1-(4-bromomethyl-phenyl)-1H-pyrazole according to the N-alkylation procedure described in Example 11: $^1$H NMR (DMSO-d$_6$) δ 8.46 (s, 1 H), 7.79 (d, 2 H, J=12.0 Hz), 7.71 (m, 3 H), 7.62 (d, 2 H, J=8.0 Hz), 7.40 (d, 2 H), J=8.0 Hz), 7.33 (s br, 1 H), 6.70 (s br, 1 H), 6.54 (s, 1 H), 4.56 (AB$_2$,2 H,Δv=16,J$_{ab}$=96 Hz), 4.00 (m, 1 H), 2.78 (m, 1 H), 2.30 (m, 1 H), 1.73 (m, 2 H), 1.37 (m, 7 H); MS m/e 509.12 (M+Na)$^+$.

EXAMPLE 24 cis-2-[(4-Chlorobenzenesulfonyl)-(4-ethylcarbamoyl-benzyl)-amino]-cycloheptanecarboxylic acid amide. cis-4-[[(2-Carbamoyl-cycloheptyl)-(4-chlorobenzenesulfonyl)-amino]-methyl]-benzoic acid methyl ester (50 mg, 0.10 mmol) and ethylamine (1.0 M in MeOH, 6 mL) were heated with stirring at 60° C. for 16 h. The solution was concentrated to dryness and the product purified by silica-gel column chromatography (20%–90% EtOAc/Hexanes) to afford 9.0 mg (18% yield) of the titled compound: 1 H NMR (DMSO-d$_6$) δ 7.89 (m, 1 H), 7.80 (d, 2 H, J=8.0 Hz), 7.72 (d, 2 H, J=8.0 Hz), 7.64 (d, 2 H, J=8.0 Hz), 7.36 (d, 2 H, J=8.0 Hz), 7.32 (s br, 1 ), 6.67 (s br, 1 H), 4.58 (AB$_2$,2 H,Δv=16,J$_{ab}$=108 Hz), 3.97 (m, 1 H), 2.76 (m, 1 H), 2.26 (m, 2 H), 1.72 (m, 2 H), 1.35 (m, 8 H), 1.12 (t, 3 H, J=8.0 Hz); MS m/e 492.29 (M+H)$^+$.

EXAMPLE 25 cis-2-[(4-Chlorobenzenesulfonyl)-(4-trifluoromethyl-benzyl)-amino]-cyclopentanecarboxylic acid amide. The titled compound (191 mg) was prepared in 50% yield from cis-2-(4-chlorobenzenesulfonylamino)-cyclopentanecarboxylic acid amide (250 mg, 0.83 mmol) and 1-bromomethyl-4-trifluoromethyl-benzene according to the N-alkylation procedure described in Example 11: $^1$ H NMR (DMSO-d$_6$) δ 7.73 (d, 2 H, J=8.0 Hz), 7.56 (m, 4 H), 7.41 (d, 2 H, J=8.0 Hz), 7.08 (s br, 1 H), 6.77 (s br, 1 H), 4.66 (AB$_2$,2 H,Δv=20,J$_{ab}$=24 Hz), 4.37 (m, 1 H), 2.85 (m, 1 H), 1.76 (m, 4 H), 1.51 (m, 2 H); MS m/e 460.98 (M+H)$^+$.

EXAMPLE 26 cis-2-[(4-Chlorobenzenesulfonyl)-(4-cyano-benzyl)-amino]-cyclopentanecarboxylic acid amide. The titled compound (68 mg) was prepared in 20% yield from cis-2-(4-Chlorobenzenesulfonylamino)-cyclopentanecarboxylic acid amide (250 mg, 0.83 mmol) and 4-bromomethyl-benzonitrile according to the N-alkylation procedure described in Example 11: $^1$H NMR (DMSO-d$_6$) δ 7.70 (d, 2 H, J=8.0 Hz), 7.71 (d, 2 H, J=12.0 Hz), 7.60 (d, 2 H, J=8.0 Hz), 7.42 (d, 2 H, J=8.0 Hz), 7.07 (s br, 1 H), 6.73 (s br, 1 H), 4.65 (AB$_2$,2 H,ΔV=20,J$_{ab}$=24 Hz), 4.33 (m, 1 H), 2.84 (m, 1 H), 1.72 (m, 4 H), 1.47 (m, 2 H); MS m/e 418.00 (M+H)$^+$.

EXAMPLE 27 cis-4-[[(2-Carbamoyl-cyclopentyl)-(4-chlorobenzenesulfonyl)-amino]-methyl]-benzoic acid methyl ester. The titled compound (161 mg) was prepared in 43% yield from cis-2-(4-chlorobenzenesulfonylamino)-cyclopentanecarboxylic acid amide (250 mg, 0.83 mmol) and methyl 4-(bromomethyl)benzoate according to the N-alkylation procedure described in Example 11: $^1$H NMR (DMSO-d$_6$) δ 7.82 (d, 2 H, J=8.0 Hz), 7.75 (d, 2 H, J=8.0 Hz), 7.58 (d, 2 H, J=8.0 Hz), 7.33 (d, 2 H, J=8.0 Hz), 7.02 (s br, 1 H), 6.75 (s br, 1 H), 4.67 (AB$_2$,2 H,Δv=20,J$_{ab}$=24 Hz), 4.33 (m, 1 H), 3.84 (s, 3 H), 2.84 (m, 1 H), 1.73 (m, 4 H), 1.48 (m, 2 H); MS m/e 451.01 (M+H)$^+$.

EXAMPLE 28

4-[[(1R,2S)-(2-Carbamoyl-cyclohexyl)-(4-chlorobenzenesulfonyl)-amino]-methyl]-N-ethyl benzamide. Cesium carbonate (1.4 mmol) was added to a solution of (1R,2S)-2-(4-Chlorobenzenesulfonylamino)-cyclohexanecarboxylic acid amide (0.62 mmol) in DMF (7 mL). 4-Chloromethyl-N-ethylbenzamide (0.76 mmol) was added to the mixture followed by potassium iodide (0.75 mmol). Reaction was stirred at room temperature overnight. Reaction mixture was diluted with ethyl acetate (20 mL) then was washed with water (2×15 mL). Organic layer was concentrated in vacuo. Residue was purified by preparatory HPLC (acetonitrile/water/trifluoroacetic acid). Proper fractions were combined. Acetonitrile was removed from the mixture in vacuo. Remaining aqueous was frozen and lyophilized to yield 4-[[(1R,2S)-(2-Carbamoyl-cyclohexyl)-(4-chlorobenzenesulfonyl)-amino]-methyl]-N-ethyl benzamide (120 mg) as a white solid in 40% yield.: $^1$H NMR (300 Mz, DMSO-d6) δ 8.40 (t, 1 H), 7.79 (d, 2 H, J=8.4), 7.70 (d, 2 H, J=8.4), 7.64 (d, 2 H, J=8.4 ), 7.32 (d, 2 H, J=8.1), 6.66 (s, 1 H), 4.68 (d, 1 H, J=17.2), 4.54 (d, 1 H, J=17.2), 3.85 (m, 1 H), 3.28 (m, 2 H), 2.78 (s, 1 H), 2.40 (m, 1 H), 1.78 (m, 1 H), 1.63 (m, 2 H), 1.42–1.17 (m, 3 H), 1.12 (t, 3 H), 0.92 (m, 1 H); MS m/e 500 (M+Na)$^+$.

EXAMPLE 29

4-[[(1S,2S)-(2-Carbamoyl-cyclohexyl)-(4-chlorobenzenesulfonyl)-amino]-methyl]-N-ethyl benzamide. (1S,2S)-2-(4-Chlorobenzenesulfonylamino)-cyclohexanecarboxylic acid amide (0.71 mmol) and 4-Chlormethyl-N-ethylbenzamide (0.86 mmol) were converted into 4-[[(1S,2S)-(2-Carbamoyl-cyclohexyl)-(4-chlorobenzenesulfonyl)-amino]-methyl]-N-ethyl benzamide following a procedure analogous to the preparation of 4-[[(1R,2S)-(2-Carbamoyl-cyclohexyl)-(4-chlorobenzenesulfonyl)-amino]-methyl]-N-ethyl benzamide. Product was obtained as a white solid in 60% yield.: $^1$H NMR (300 Mz, DMSO-d6) δ 8.43 (t, 1 H, J=5.5), 7.71 (d, 4 H, J=8.4), 7.51 (d, 2 H, J=8.4), 7.45 (d, 2 H, J=8.0), 7.34 (s, 1 H), 6.76 (s, 1 H), 4.50 (d, 1 H, J=15.7), 4.30 (d, 1 H, J=15.7), 3.91 (m, 1 H), 3.28 (m, 3 H), 1.80 (m,1 H), 1.56 (m, 3 H), 1.35 (m, 1 H), 1.17 (m, 2 H), 1.12 (t, 3 H, J=7.0), 0.95 (m, 1 H); MS m/e 478 (M+H)$^+$.

EXAMPLE 30

4-[[(1R,2R)-(2-Carbamoyl-cyclohexyl)-(4-chlorobenzenesulfonyl)-amino]-methyl]-N-ethyl benzamide. (1R,2R)-2-(4-Chlorobenzenesulfonylamino)-cyclohexanecarboxylic acid amide (0.39 mmol) and 4-Chlormethyl-N-ethylbenzamide (0.48 mmol) were converted to 4-[[(1R,2R)-(2-Carbamoyl-cyclohexyl)-(4-chlorobenzenesulfonyl)-amino]-methyl]-N-ethyl benzamide following a procedure analogous to the preparation of 4-[[(1R,2S)-(2-Carbamoyl-cyclohexyl)-(4-chlorobenzenesulfonyl)-amino]-methyl]-N-ethyl benzamide. Product was obtained as a white solid in 69% yield.: $^1$ H NMR (300 Mz, DMSO-d6) δ 8.43 (t, 1 H, J=5.5), 7.71 (d, 4 H, J=8.4), 7.51 (d, 2 H, J=8.4), 7.45 (d, 2 H, J=8.0), 7.34 (s, 1 H), 6.76 (s, 1 H), 4.50 (d, 1 H, J=15.7), 4.30 (d, 1 H, J=15.7), 3.91 (m, 1 H), 3.28 (m, 3 H), 1.80 (m,1 H), 1.56 (m, 3 H), 1.35 (m, 1 H), 1.17 (m, 2 H), 1.12 (t, 3 H, J=7.0), 0.95 (m, 1 H); MS m/e 500 (M+Na)$^+$.

EXAMPLE 31

4-[[(1R,2S)-(2-Carbamoyl-cyclopentyl)-(4-chlorobenzenesulfonyl)-amino]-methyl]-N-ethyl-benzamide. The titled compound was prepared analogous to Example 30 in 5 steps from methyl-1-cyclopentenecarboxylate and R-(+)-N-benzyl-α-methylbenzylamine. The product was obtained as a white powder.: $^1$H NMR (300 Mz, DMSO-d6) δ 8.38 (t, 1 H, J=5.5 Hz), 7.75 (d, 2 H, J=8.8 Hz), 7.70 (d, 2 H, J=8.4 Hz), 7.57 (d, 2 H, J=8.8 Hz), 7.24 (d, 2 H, J=8.4 Hz), 7.00 (s, 1 H), 6.75 (br s, 1 H), 4.65 (m, 2 H), 4.30 (m, 1 H), 3.28 (m, 2 H), 2.84 (m, 1 H), 1.90–1.40 (m, 6 H), 1.12 (t, 3 H, J=6.9 Hz); MS m/e 464.3 (M+H)$^+$.

EXAMPLE 32

4-[[(1R,2R)-(2-Carbamoyl-cyclopentyl)-(4-chlorobenzenesulfonyl)-amino]-methyl]-N-ethyl-benzamide. The titled compound was prepared analogous to Example 31 in 6 steps from methyl-1-cyclopentenecarboxylate and R-(+)-N-benzyl-α-methylbenzylamine. The product was obtained as a white powder.: $^1$H NMR (300 Mz, DMSO-d6) δ 8.42 (t, 1 H, J=5.5 Hz), 7.82 (d, 2 H, J=8.4 Hz), 7.79 (d, 2 H, J=6.9 Hz), 7.62 (d, 2 H, J=8.4), 7.43 (d, 2 H, J=7.4 Hz), 7.07 (s, 1 H), 6.73 (br s, 1 H), 4.57 (m, 1 H), 4.41 (m, 2 H), 3.29 (m, 2 H), 2.57 (m, 1 H), 1.85–1.20 (m, 6 H), 1.12 (t, 3 H, J=7.3 Hz); MS m/e 464.3 (M+H)$^+$.

We claim:
1. A compound of Formula I or a stereoisomer thereof

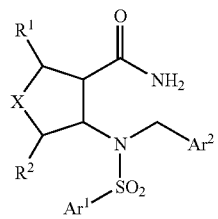

I wherein:

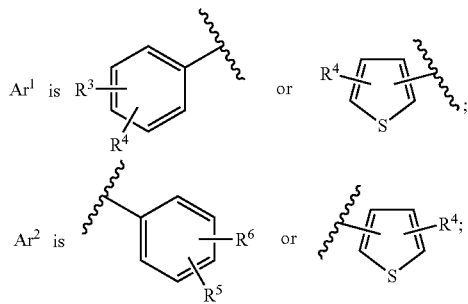

X is methylene, ethylene, propylene, 1,2-ethenediyl, or 1,2-cyclopropanediyl;
$R^1$ and $R^2$ are independently hydrogen or $C_{1-6}$alkyl or taken together are methylene or ethylene;
$R^3$ is halogen;
$R^4$ is hydrogen or halogen;
$R^5$ is halogen, $C_{1-6}$alkyl, $C_{1-3}$alkoxy, $C_{1-3}$hydroxyalkyl, trifluoromethyl, trifluoromethoxy, trifluoromethylthio, cyano, $CO_2R^7$, $CONR^8R^9$, $NR^8R^9$, or $N(R^7)COR^7$;
$R^6$ is hydrogen, halogen, $C_{1-6}$alkyl, $C_{1-3}$alkoxy, cyano, trifluoromethyl, or trifluoromethoxy;
$R^7$ is hydrogen or $C_{1-6}$alkyl; and
$R^8$ and $R^9$ are independently hydrogen or $C_{1-6}$alkyl;
or a pharmaceutically acceptable salt or solvate thereof.

2. A compound of claim 1 wherein $Ar^1$ is 4-chlorophenyl.

3. A compound of claim 2 selected from the group consisting of
cis-exo-3-[(4-chloro-benzenesulfonyl)-(4-trifluoromethyl-benzyl)-amino]-bicyclo[2.2.1]heptane-2-carboxylic acid amide;
cis-exo-3-[(4-chloro-benzenesulfonyl)-(4-cyano-benzyl)-amino]-bicyclo[2.2.1]heptane-2-carboxylic acid amide;
cis-exo-4-[[(3-carbamoyl-bicyclo[2.2.1]hept-2-yl)-(4-chloro-benzenesulfonyl)-amino]-methyl]-benzoic acid methyl ester;
cis-4-[[(2-carbamoyl-cycloheptyl)-(4-chloro-benzenesulfonyl)-amino]-methyl]-benzoic acid methyl ester;
cis-2-[(4-chloro-benzenesulfonyl)-(4-cyano-benzyl)-amino]-cycloheptanecarboxylic acid amide;
cis-2-[(4-chloro-benzenesulfonyl)-(4-trifluoromethyl-benzyl)-amino]-cycloheptanecarboxylic acid amide;
cis-2-[(4-chloro-benzenesulfonyl)-(4-pyrazol-1-yl-benzyl)-amino]-cycloheptanecarboxylic acid amide;
cis-2-[(4-chloro-benzenesulfonyl)-(4-ethylcarbamoyl-benzyl)-amino]-cycloheptanecarboxylic acid amide;
cis-2-[(4-chloro-benzenesulfonyl)-(4-trifluoromethyl-benzyl)-amino]-cyclopentanecarboxylic acid amide;
cis-2-[(4-chloro-benzenesulfonyl)-(4-cyano-benzyl)-amino]-cyclopentanecarboxylic acid amide;
cis-4-[[(2-carbamoyl-cyclopentyl)-(4-chloro-benzenesulfonyl)-amino]-methyl]-benzoic acid methyl ester;
4-[[(1R,2S)-(2-carbamoyl-cyclopentyl)-(4-chlorobenzenesulfonyl)-amino]-methyl]-N-ethyl-benzamide;
4-[[(1R,2R)-(2-carbamoyl-cyclopentyl)-(4-chlorobenzenesulfonyl)-amino]-methyl]-N-ethyl-benzamide;
cis-2-[(4-chloro-benzenesulfonyl)-(4-trifluoromethoxy-benzyl)-amino]-cyclohexanecarboxylic acid amide;
cis-2-[(4-chloro-benzenesulfonyl)-(4-trifluoromethyl-benzyl)-amino]-cyclohexanecarboxylic acid amide;
cis-2-[(4-chloro-benzenesulfonyl)-(4-fluoro-benzyl)-amino]-cyclohexanecarboxylic acid amide;
cis-2-[(4-chloro-benzenesulfonyl)-(4-cyano-benzyl)-amino]-cyclohexanecarboxylic acid amide;
cis-4-[[(2-carbamoyl-cyclohexyl)-(4-chloro-benzenesulfonyl)-amino]-methyl]-benzoic acid methyl ester;
trans-2-[(4-chloro-benzenesulfonyl)-(4-trifluoromethoxy-benzyl)-amino]-cyclohexanecarboxylic acid amide;
trans-2-[(4-chloro-benzenesulfonyl)-(4-trifluoromethyl-benzyl)-amino]-cyclohexanecarboxylic acid amide;
trans-2-[(4-chloro-benzenesulfonyl)-(4-cyano-benzyl)-amino]-cyclohexanecarboxylic acid amide;
(1S,2R)-2-[(4-tert-butyl-benzyl)-(4-chloro-benzenesulfonyl)-amino]-cyclohexanecarboxylic acid amide;
(1S,2R)-2-[(4-chloro-benzenesulfonyl)-(3-chloro-4-trifluoromethoxy-benzyl)-amino]-cyclohexanecarboxylic acid amide;
(1S,2R)-2-[(4-chloro-benzenesulfonyl)-(3-chloro-4-fluoro-benzyl)-amino]-cyclohexanecarboxylic acid amide;
(1S,2R)-2-[(4-chloro-benzenesulfonyl)-[4-(1-hydroxy-1-methyl-ethyl)-benzyl]-amino]-cyclohexanecarboxylic acid amide;
(1S,2R)-2-[(4-chloro-benzenesulfonyl)-(5-chloro-thiophen-2-ylmethyl)-amino]-cyclohexanecarboxylic acid amide;
(1S,2R)-2-[(4-chloro-benzenesulfonyl)-(4-trifluoromethylsulfanyl-benzyl)-amino]-cyclohexanecarboxylic acid amide;
4-[[(1S,2S)-(2-carbamoyl-cyclohexyl)-(4-chlorobenzenesulfonyl)-amino]-methyl]-N-ethyl benzamide; and 4-[[(1R,2R)-(2-carbamoyl-cyclohexyl)-(4-chlorobenzenesulfonyl)-amino]-methyl]-N-ethyl benzamide;
or a pharmaceutically acceptable salt or solvate thereof.

4. A compound of claim 1 as defined by Formula Ia.

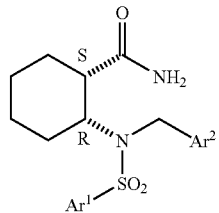

5. A compound of claim 4 selected from the group consisting of
4-[[(1R,2S)-(2-carbamoyl-cyclohexyl)-(4-chloro-benzenesulfonyl)-amino]-methyl]-benzoic acid methyl ester;
4-[[(1R,2S)-(2-carbamoyl-cyclohexyl)-(4-chloro-benzenesulfonyl)-amino]-methyl]-N-ethyl-benzamide; and
4-[[(1R,2S)-(2-carbamoyl-cyclohexyl)-(4-chlorobenzenesulfonyl)-amino]-methyl]-N-ethyl benzamide;
or a pharmaceutically acceptable salt or solvate thereof.

6. A pharmaceutical composition for the treatment of disorders responsive to the inhibition of β-amyloid peptide production comprising a therapeutically effective amount of a compound of claim 1 and a pharmaceutically acceptable carrier or diluent.

7. A method for the treatment of disorders responsive to the inhibition of β-amyloid peptide production in a patient in need thereof, comprising administering a therapeutically effective amount of a compound of claim 1 to the patient.

8. The method of claim 7 wherein the disorder is Alzheimer's Disease or Down's Syndrome.

* * * * *